United States Patent [19]

Boyd

[11] 4,138,721
[45] Feb. 6, 1979

[54] LIMITED SCAN ANGLE FAN BEAM COMPUTERIZED TOMOGRAPHY

[75] Inventor: Douglas P. Boyd, Woodside, Calif.

[73] Assignee: Board of Trustees of The Lelane Standard Junior University, Stanford, Calif.

[21] Appl. No.: 741,128

[22] Filed: Nov. 11, 1976

[51] Int. Cl.² .......................................... G01M 23/00
[52] U.S. Cl. ................................. 364/414; 250/363 S; 250/445 T
[58] Field of Search ..................... 235/151.3; 250/362, 250/363 R, 366, 445 T, 445 R; 364/414, 300, 200, 900

[56] References Cited

U.S. PATENT DOCUMENTS

| | | | |
|---|---|---|---|
| 4,002,911 | 1/1977 | Hounsfield | 250/445 T |
| 4,008,400 | 2/1977 | Brunnett et al. | 250/445 T |
| 4,010,370 | 3/1977 | Le May | 235/151.3 |
| 4,032,761 | 6/1977 | Mayo et al. | 235/151.3 |

OTHER PUBLICATIONS

Chu, Z. H.; General Views on 3-D Image Reconstruction and Computerized Transverse Axial Tomography; IEEE Trans. on Nuclear Science, vol. NS-21, Jun. 1974, pp. 44–70.

EMI Handbook; EMI-Scanner CT 1010-The Second-Generation Diagnostic System for Neuroradiological Examinations; Nov. 1975.

*Primary Examiner*—Malcolm A. Morrison
*Assistant Examiner*—Errol A. Krass

[57] ABSTRACT

A fan-shaped beam or a fan array of individual beamlets of penetrating radiation, such as X-ray or γ-ray radiation, is directed through a planar slice of the body to be analyzed to a position sensitive detector. The fan beam and the detector are caused to move in a rectilinear or nearly rectilinear fashion so that the individual beamlets or rays of penetrating radiation scan across the body and each detector records a parallel ray shadowgraph at a different angle of rotation (scan angle) with respect to the body and covering a range of scan angles less than 180° and typically approximately 90°. The recorded shadowgraphic data is then reconstructed into a 3-D tomograph of the body using a method of successive approximations. The resultant scanner may be used to analyze planes of the body parallel to the major axis thereof such as saggital or coronal as well as transaxial planes. In a preferred embodiment, the position sensitive detector includes detector elements arranged for detecting penetrating radiation passing through the body in a number of divergent planes diverging from the source. 3-D tomographs are reconstructed from the corresponding divergent plane shadowgraphic data. An advantage in use of the scanner of the present invention is that faster scan times are achieved due to the rectilinear or nearly rectilinear translation of the scanner which enables a reduction of blurring of the resultant tomographs due to biological motion. A further advantage is that multiple planes may be scanned simultaneously.

30 Claims, 16 Drawing Figures

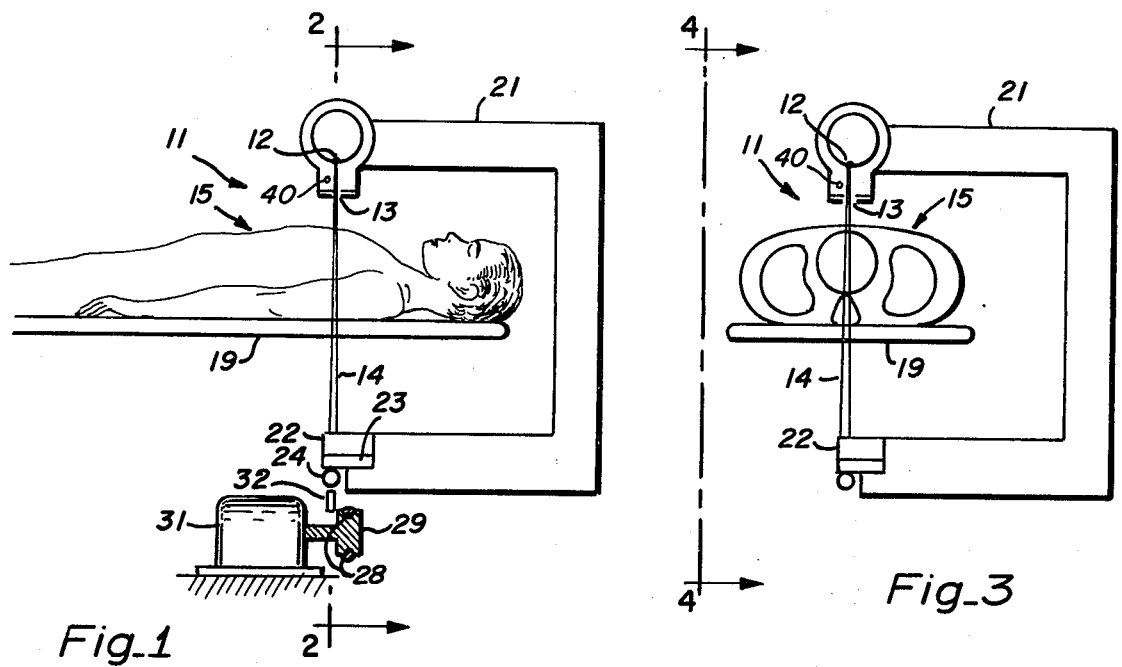
Fig. 1
Fig. 3
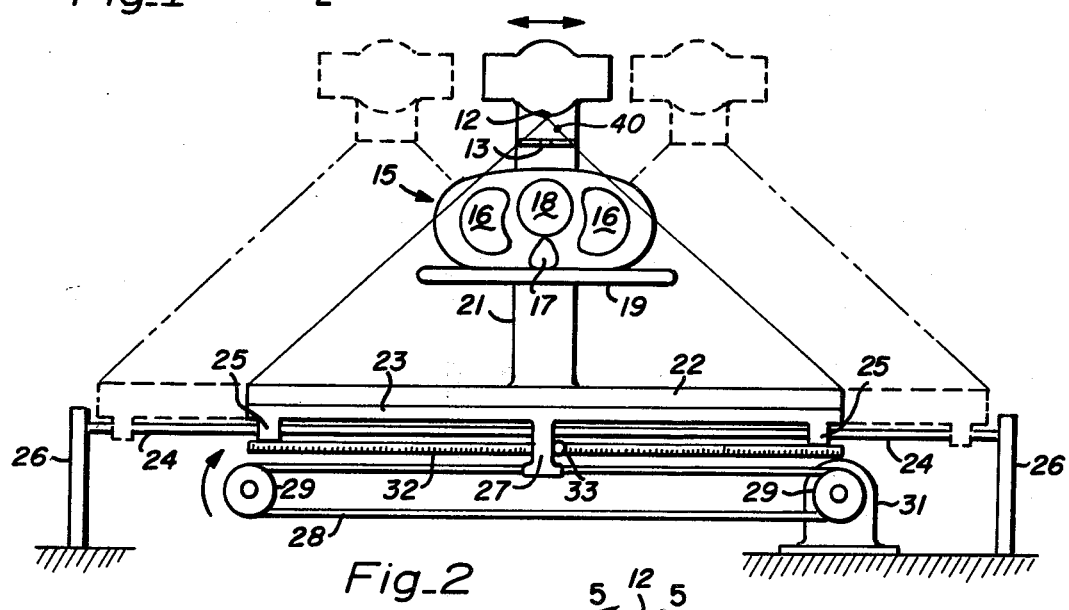
Fig. 2
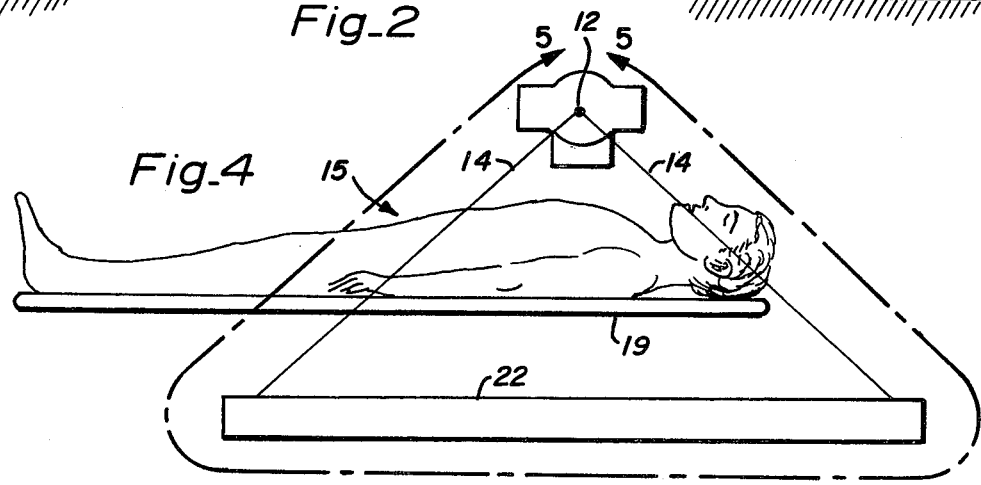
Fig. 4

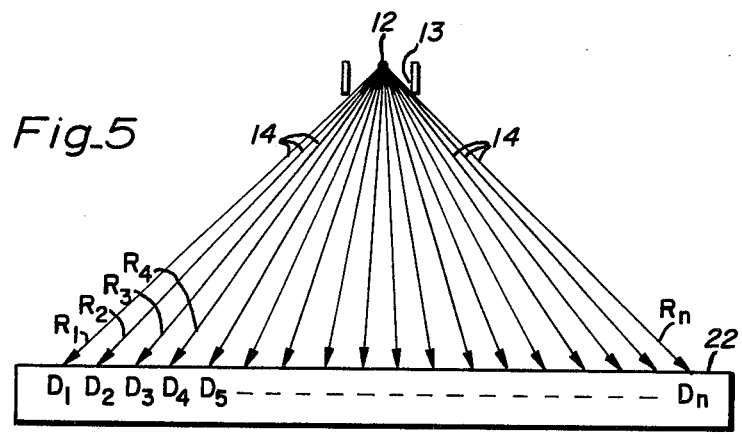
Fig_5
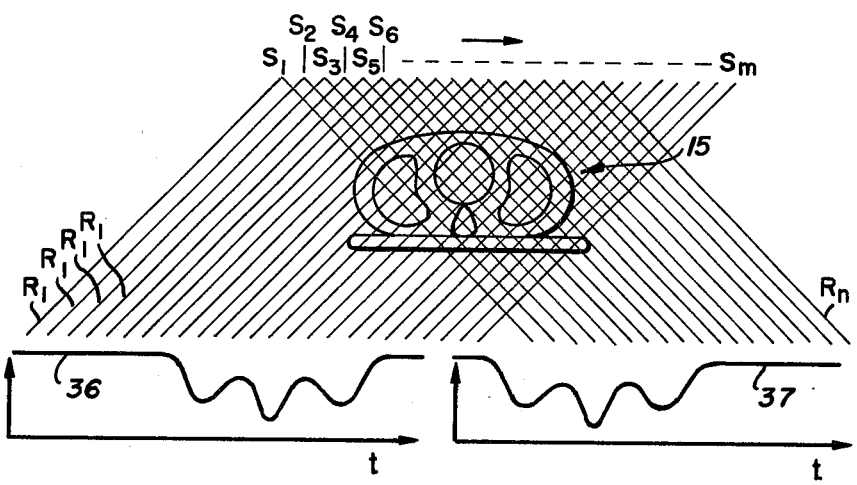
Fig_6
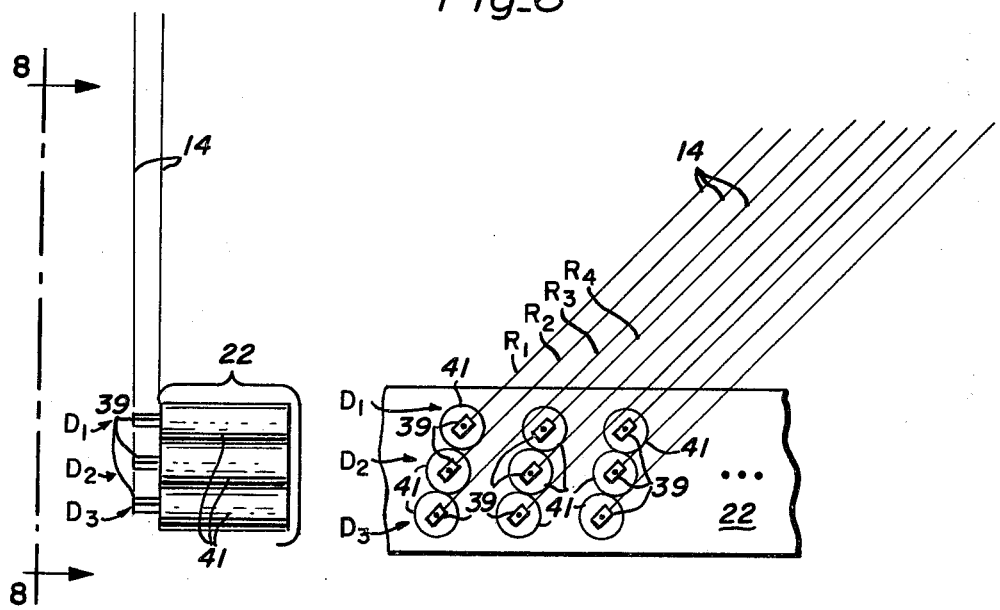
Fig_7   Fig_8

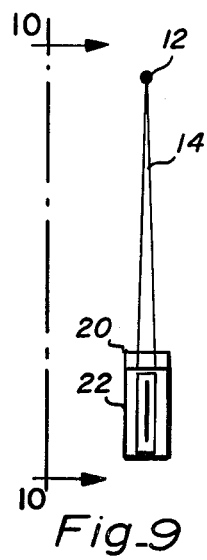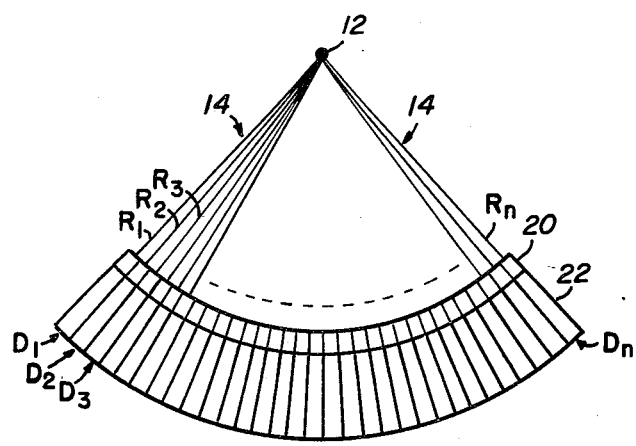
Fig_9    Fig_10
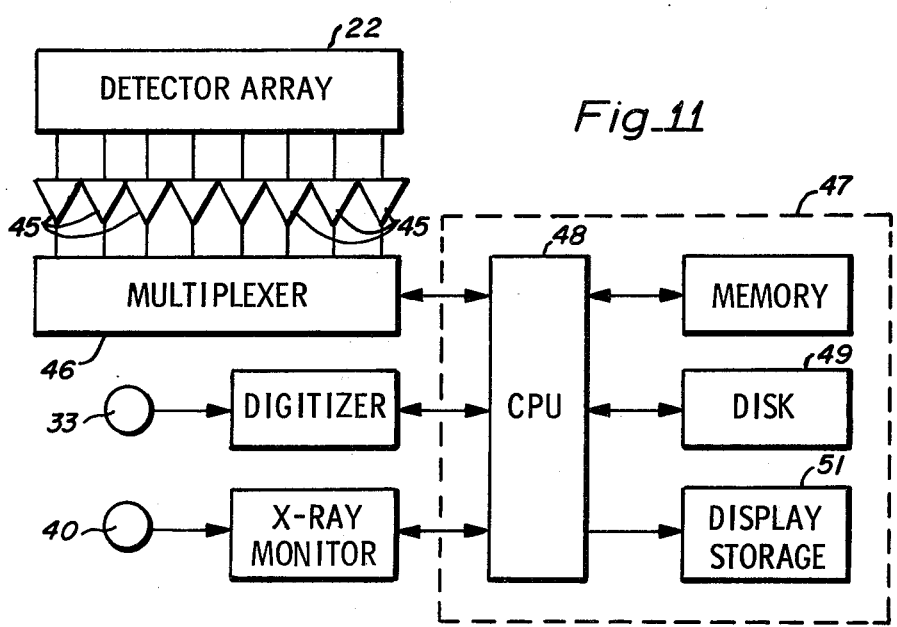
Fig_11
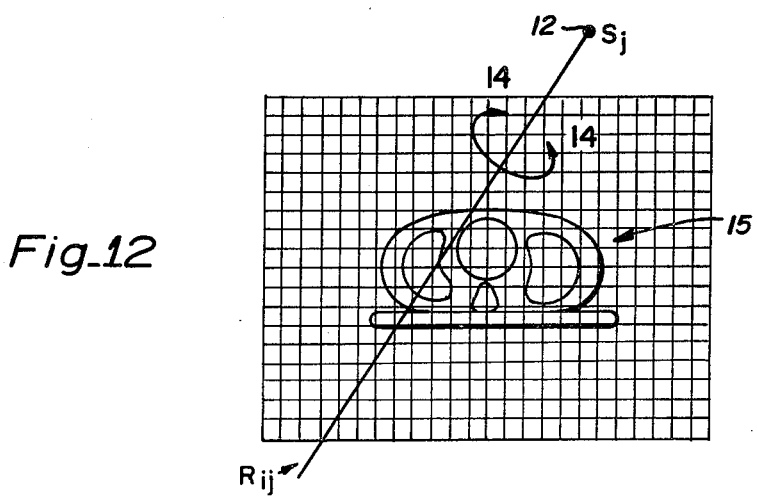
Fig_12

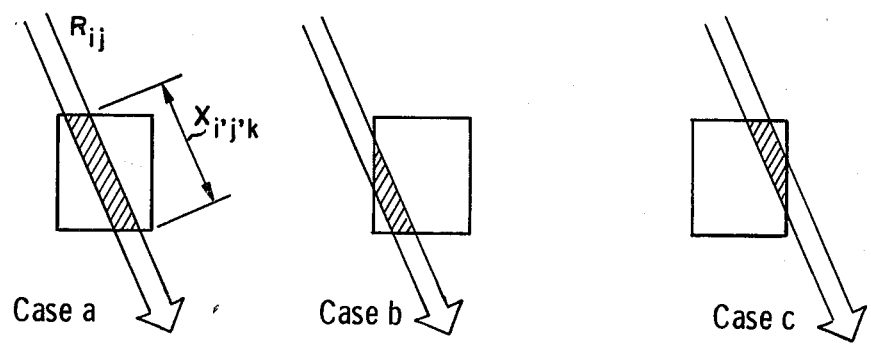
Fig_13
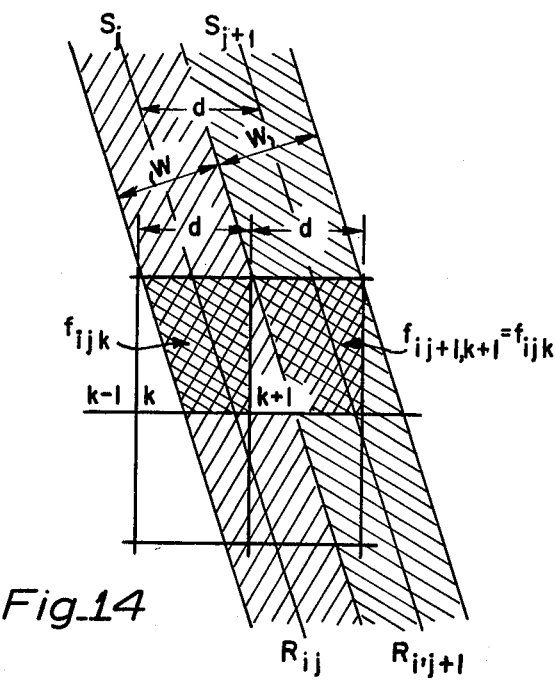
Fig_14
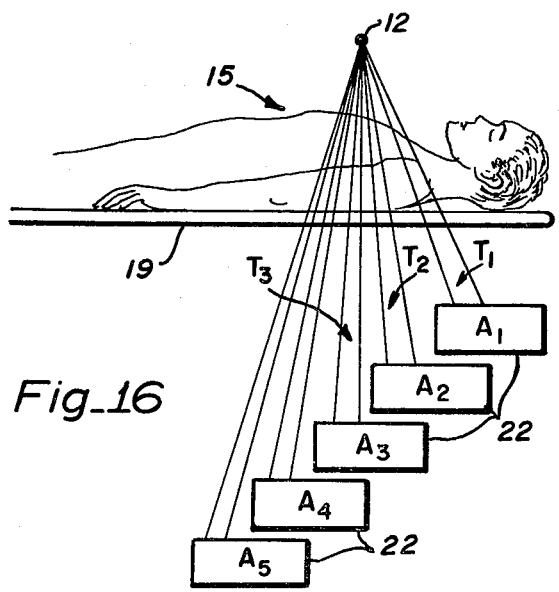
Fig_16
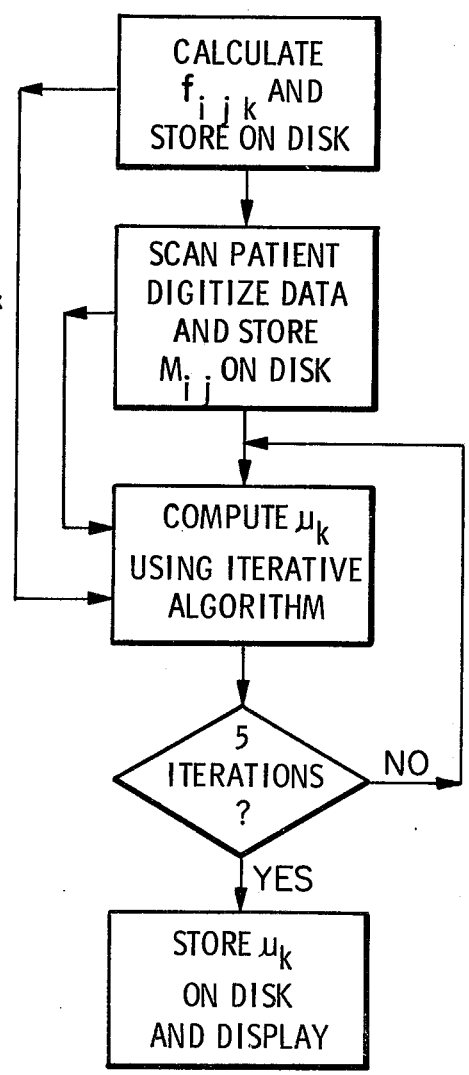
Fig_15 ns. 4,138,721

LIMITED SCAN ANGLE FAN BEAM COMPUTERIZED TOMOGRAPHY

GOVERNMENT CONTRACT

The Government has rights in this invention pursuant to Grant No. GI-35007 awarded by the National Science Foundation.

BACKGROUND OF THE INVENTION

The present invention relates in general to fan beam or beamlet X-ray or $\gamma$-ray 3-D tomography and more particularly to such tomography utilizing a position sensitive detector and a computer for reconstruction of the 3-D tomographs.

DESCRIPTION OF THE PRIOR ART

Heretofore, a fan-shaped beam of penetrating radiation, such as X-ray or $\gamma$-ray radiation, has been directed through a planar slice of the body to be analyzed to a position sensitive detector for deriving a shadowgraph of transmission or absorption of the penetrating radiation by the body. A number of shadowgraphs are obtained for different angles of rotation (scan angles) of the fan-shaped beam relative to the center of the slice being analyzed. The detected fan beam shadowgraph data was re-ordered into shadowgraphic data corresponding to sets of parallel paths of radiation through the body, the re-ordered parallel path shadowgraph data was then back projected in accordance with a 3-D reconstruction method of convolution in a computer to derive a 3-D reconstructed tomograph of the body under analysis for a given planar slice therethrough.

In a preferred embodiment, the position sensitive detector comprised a multiwave xenon gas-filled detector wherein the wires were arrayed parallel to the direction of the divergent penetrating rays to be detected. The focusing grid collimator was interposed between the body and the position sensitive detector for collimating the penetrating rays to be detected. The source of penetrating radiation was preferably a monochromatic source. Such a fan beam computerized tomographic apparatus is disclosed and claimed in U.S. Patent Application Ser. No. 528,026 now U.S. Pat. No. 4,075,492 filed Nov. 29, 1974, and U.S. Pat. No. 3,983,398, both assigned to the same assignee as the present invention.

It has also been proposed to employ collimated beams of penetrating radiation to derive a set of angularly displaced shadowgraphic data from which to construct a 3-D tomograph of a planar slice of a body under analysis. The 3-D tomograph was reconstructed by a computer using a method of back projecting the shadowgraphic data by a process of successive approximations to derive the final 3-D tomograph. Such a method is proposed in U.S. Pat. No. 3,778,614 issued Dec. 11, 1973.

In this latter patent a single collimated beamlet of penetrating radiation is passed through the body to a detector in alignment with the beam path. The single detector and single source are then rectilinearly translated. laterally relative to the body to derive a given set of parallel ray shadowgraphic data for a given scan angle. The source and detector are then angularly rotated to a second scan angle in the plane under analysis and then laterally translated relative to the body to obtain a second set of shadowgraphic data for a second scan angle, and so forth. This is continued for 180° of rotation to derive 180 shadowgraphs which are back projected.

In a second method, proposed in U.S. Pat. No. 3,946,234 issued Mar. 23, 1976, a fan-shaped array of collimated beamlets of penetrating radiation, each beamlet having a detector in alignment therewith, is caused to be laterally rectilinearly translated relative to the body and then rotated to a second scan angle with lateral translation at the second scan angle, and so forth and so on, to derive sets of shadowgraphic data for a plurality of scan angles.

Thus, in the prior art there are two types of computerized tomographic scanners which have achieved wide usage. One type of scanner is that exemplified bu U.S. Pat. Nos. 3,778,614 and 3,946,234 and may be referred to as a two-motion system. That is, the scanner is translated rectilinearly laterally relative to the body for a given scan angle and then rotated in increments of scan angle around the body to obtain a complete set of shadowgraphic data for computerized reconstruction of the tomograph. The second class of scanners, as exemplified by U.S. Pat. application No. 528,026 and U.S. Pat. No. 3,983,398, employs a fan beam of x-rays and involves pure rotary motion about the body. The advantage of the rotary fan beam scanner over the two-motion scanner is that greater utilization of the source intensity is obtained and mechanical simplicity offers greater scanning speed.

However, rotary fan beam scanners have the disadvantage that far greater detector stability is required since the detectors cannot be calibrated immediately preceding the scan as in the two-motion lateral system. In addition, the particular scanning geometry of a rotary fan beam scanner tends to concentrate small errors, produced by a particular detector in the detector array, into a relatively small arc-shaped region of the tomograph thereby creating artifacts in the resultant 3-D tomograph and this sets a further more stringent stability requirement for the detectors in a pure rotary fan beam scanner.

Due to the presence of substantial centrifugal forces in a pure rotary scanner it is unlikely that their scanning speed can be reduced to times less than one second. This is a disadvantage when trying to obtain a 3-D tomograph of certain biologically moving organs such as the heart, blood flow and the like. In order to image such moving organs, a total scanning time of less than one-tenth of a second is desired. The prior art scanner which utilizes a combination of both lateral and rotary motion is slower than a pure rotary system and thus also is an unlikely candidate for 3-D tomograph of moving organs.

Recently American Science and Engineering of Cambridge, Massachusetts, has announced a third class of scanner. This scanner employs a pure rotary fan beam of X-ray radiation which is detected by a stationary array of 600 detectors arranged in a circular ring about the body. This configuration effectively solves the stability requirement associated with pure rotary fan beam scanners since calibration is possible and the arc-shaped artifact problem should be solved with this class of a scanner. However, a disadvantage is that many more detectors are required for this configuration than for either the combined rectilinear and rotary scan or for the pure rotary scan.

None of the above three classes of scanners have the ability to scan a large number of adjacent slices simultaneously. This is definitely desired for 3-D tomography of moving organs or for observing the movement of blood within various organs of the body. Nor can the three aforementioned classes of scanners conveniently scan planes other than those that are transverse to the body axis. Centrifugal forces and the great distances traveled by the source make very short scan times infeasible.

SUMMARY OF THE PRESENT INVENTION

The principal object of the present invention is the provision of an improved method and apparatus for reconstructing 3-D tomographs of a body under analysis.

In one feature of the present invention, penetrating radiation, such as X-rays or γ-rays, is directed through the body under analysis over a set of divergent paths for a given scan angle and the scan angle is changed preferably along a rectilinear or nearly rectilinear path to derive sets of shadowgraphic data. A 3-D tomograph of a planar slice of the body under analysis is reconstructed from only a limited number of the sets of shadowgraphic data corresponding to a total scan angle of substantially less than 180°, generally on the order of 60°-130°, whereby the scan time can be substantially reduced.

In another feature of the present invention, the source is caused to traverse a locus of points relative to the body falling essentially only on a line having a radius of curvature substantially larger, including infinity, than the distance from the source to the center of the body under analysis, whereby an essentially rectilinear translation of the source relative to the body is obtained, thereby greatly reducing the scan time.

In another feature of the present invention, the divergent penetrating radiation is passed through the body and is detected in a plurality of divergent planar slices, such planar slices intersecting at the locus of points defining the path of movement of the source relative to the body, whereby several planes in the body may be scanned simultaneously with short scan times.

In another feature of the present invention, the detected ray spacing is chosen to be approximately equal to or a harmonic of a cell width of the tomographic three-D reconstruction matrix, whereby the data storage and computations are greatly simplified.

Other features and advantages of the present invention will become apparent upon a perusal of the following specification taken in connection with the accompanying drawings wherein:

BRIEF DESCRIPTION OF THE DRAWINGS

FIG. 1 is a side elevational view, partly schematic, of a computerized tomographic scanner incorporating features of the present invention, FIG. 2 is a sectional view of the structure of FIG. 1 taken along line 2—2 in the direction of the arrows, FIG. 3 is a view similar to that of FIG. 1 with the patient rotated 90° for a coronal scan, FIG. 4 is a elevational view of the structure of FIG. 3 taken along line 4—4 in the direction of the arrows, FIG. 5 is a schematic representation of a portion of the structure of FIG. 4 delineated by line 5—5 and depicting the paths of divergent penetrating radiation passing through the body to the detector array, FIG. 6 is a schematic diagram depicting the fan beam of penetrating radiation in the plane of the fan and illustrating the manner in which parallel ray shadowgraphic data are derived, FIG. 7 is a side elevational view of a detector array employing scintillation crystal photomultipliers, FIG. 8 is a partial foreshortened view of the structure of FIG. 7 taken along line 8—8 in the direction of the arrows, FIG. 9 is a view similar to that of FIG. 7 depicting an alternative gas ionization detector array, FIG. 10 is a side view of the structure of FIG. 9 taken along line 10—10 in the direction of the arrows, FIG. 11 is a circuit diagram, in block diagram form, of a data acquisition and processing system utilized in the scanner of FIGS. 1 and 2, FIG. 12 shows the division of the tomographic image into a reconstruction matrix of attenuation coefficients $\mu_k$ and the path of a particular ray $R_i$, $S_j$ through the matrix, FIG. 13 shows in cases a, b and c, three possible examples in which the matrix cell intersection $X_{ijk}$ may need to be calculated, FIG. 14 is an expanded view of a portion of the reconstruction matrix of FIG. 12 depicting adjacent cells being intercepted by adjacent parallel rays for successive positions of the X-ray source and showing the relationship of cell width to beam width, FIG. 15 is a computer flow chart for the computer reconstruction program utilized in the system of FIGS. 1 and 2, and FIG. 16 shows the manner in which several tomographic slices $t_1...t_s$ may be scanned simultaneously utilizing the scanner system of the present invention.

DESCRIPTION OF THE PREFERRED EMBODIMENTS

Referring now to FIGS. 1 and 2 there is shown a rectilinear limited scan angle computerized tomographic body scanner 11 incorporating features of the present invention. The scanner 11 includes a source of penetrating radiation 12, such as X-ray or γ-ray radiation. A suitable source 12 is a rotating anode diagnostic X-ray tube. The X-rays emitted from the tube 12 are collimated into a fan-shaped beam of radiation by passing the X-rays from the source 12 through an elongated slot-shaped aperture 13 in an X-ray shield structure. The fan-shaped beam of radiation 14, which may also comprise a fan-shaped array of individual X-ray beamlets, as derived by passing the X-rays from the source 12 through a plurality of divergent bores in a lead shield, arranged in a fan-shaped array radiating away from the source 12. The fan-shaped beam of X-rays 14 is directed through a transaxial section of a body 15 under analysis. A particular transaxial section is shown in FIGS. 1 and 2 and includes a section of the lungs 16, spine 17, and heart 18, respectively. The body 15 is resting on a couch 19 of low X-ray absorption material, as of plastic.

The X-ray source 12 is rigidly mounted to a C-shaped beam structure 21 and an X-ray detector array 22 is rigidly affixed to the end of the C-shaped beam 21 opposite to that to which the X-ray tube 12 is affixed. In a typical example, the detector array 22 may comprise a xenon filled multiwire detector of the type disclosed and claimed in copending U.S. patent application Ser. No. 528,025, now abandoned filed Nov. 29, 1974, which is more fully disclosed below relative to FIG. 10. As an alternative, the detector array 22 may comprise an array of scintillator crystals affixed to photomultiplier tubes in the manner as more fully described below with regard to FIGS. 7 and 8.

The detector array 22 forms a position sensitive detector and thus serves to detect the intensity of the X-rays incident thereon as a function of the angle subtended by the fan-shaped beam 14. The detector array 22 is carried from the C-shaped support 21 via a transverse beam 23 extending perpendicularly to the lower leg of the C-shaped beam 21. The transverse beam 23 is slideably supported from a precision ground elongated rod 24 via the intermediary of three ball-bearing assemblies 25. The fixed support rod 24 is rigidly secured to a fixed support structure 26 at opposite ends thereof. A central bracket 27 serves to couple the transverse beam 23 and thus the C-shaped carrier support to a drive belt 28 for driving the source 12 and detector array 22 together with the C-shaped beam 21 to and fro on the rod 24. The drive belt 28 rides on a pair of pulleys 29 at opposite ends thereof. One of the pulleys 29 is driven from an electrical motor 31. The motor 31 and pulleys 29 are supported from a fixed platform.

A linear graticule 32 is fixedly secured to the fixed platform and a photocell 33, which is carried from the bracket 27, views the scale on the linear graticule 32 to derive an output indicative of the position of the X-ray source 12 and detector array 22 relative to the fixed platform. The couch 19 which supports the patient is also fixed to the fixed platform so that the X-ray source 12 and detector array 22 move to and fro along a rectilinear locus of points across the body 15, as indicated in FIG. 2 by the phantom lines showing the opposite extremes of travel of the X-ray source 12 and detector 22.

Referring now to FIGS. 3 and 4 there is shown the system of the scanner 11 of FIGS. 1 and 2 as employed for scanning a coronal plane of the body 15. In this embodiment, the couch 19 has been turned 90° to its position in FIGS. 1 and 2.

FIG. 5 shows the manner in which the fan-shaped beam of penetrating radiation 14 may be considered as being sub-divided into an array of divergent penetrating rays within the fanshaped beam 14. The rays are labeled $R_1, R_2, \ldots R_n$ from left to right. A preferred number of $n$ of rays is 180 or more. A suitable fan angle $\theta$ from an x-ray tube is on the order of 60°–130°, generally approximately 90°. Each ray is detected by a particular element of the detector array 22 as indicated at $D_1, D_2 \ldots D_n$. The detector array 22 can include a focusing grid collimator integral therewith or between the array 22 and body 15 for collimating the penetrating radiation reaching the individual detectors $D_1 \ldots D_n$ along ray lines $R_1 \ldots R_n$ respectively. This is more fully described in copending U.S. application Ser. No. 528,025, now abandoned filed Nov. 29, 1974; see also U.S. Pat. No. 3,983,398. However, in many cases a focusing grid collimator will not be necessary to reduce the effects of scattered radiation. Firstly, when the beam is collimated into a fan shape, as with collimator 13, the amount of scattered X-rays generated are considerably reduced as compared to conventional radiography. In addition, the air space between the body and the detector can reduce the scattered radiation sufficiently to render its effects negligible.

Referring now to FIG. 6 it is shown that as the source moves linearly through a number of positions $S_1, S_2 \ldots$ each of the detectors $D_1, D_2 \ldots D_n$ detects shadowgraphic data corresponding to a parallel ray shadowgram of the planar slice of the body under analysis, each detector corresponding to a different scan angle determined by the angle from the source to the respective detector. In a preferred embodiment there are 600 or more source positions $m$. The source positions $S_i$ are determined by the position read out by the photocell 33 from the graticule 32. These source positions may be defined by pulsing the X-ray source 12 at appropriate times or if a continuous source 12 is used then by integrating the outputs of the detectors over time intervals corresponding to the respective source movements.

The shadowgram output for a first detector $D_1$ of detector 22 and which corresponds to ray $R_1$ is shown by shadowgram 36, whereas the shadowgram output of the last detector $D_n$ corresponding to ray $R_n$ is shown by shadowgram 37. The intermediate detectors each detect a shadowgram corresponding to their individual different scan angles. The shadowgrams are a plot of X-ray intensity viewed by the respective detector as the source 12 scans from $S_1$ to $S_m$ and represents the integral X-ray attenuation of the body as the beam sweeps across the plane-shaped sector or matrix under analysis. Altogether, there are $n$ number of shadowgrams at $n$ number of view angles, each shadowgram having $m$ number of data points. These different shadowgraphic data represent shadowgrams of parallel ray data and this parallel ray data is detected and stored in the memory of a computer for subsequent reconstruction of a 3-D X-ray tomograph in the manner to be more fully described below.

Referring now to FIGS. 7 and 8 there is shown a detector array employing scintillation detector elements 39, such as NaI crystal scintillators, coupled to the photomultiplier tubes 41. The crystal detectors 39 are elongated and oriented with their longitudinal axes in alignment with the respective rays to be detected. The respective detectors 39 are arranged in staggered relation so as to intercept the respective rays $R_1 \ldots R_n$. In a typical example, the scintillation crystals 39 have a width of ¾ inch and they are arranged in groups of three in three rows as indicated in order to achieve a ray spacing of ¼ inch.

Referring now to FIGS. 9 and 10 there is shown an alternative xenon multiwire detector array of the type disclosed and claimed in the aforecited pending application Ser. No. 528,025, now abandoned. Briefly, the detector array consists of an array of gas ionization chambers whose electrodes are elongated and directed radial to the source 12. As aforementioned, a focusing grid collimator 20, if required for suppression of scattered radiation, radially collimates the x-rays from the body 15 into the detectors $D_1 \ldots D_n$.

Referring now to FIG. 11, the output of each detector of the detector array 22 is an electrical current having a value linearly related to the detected X-ray intensity. These currents are amplified by amplifiers 45 and then sampled and digitized by a multiplexer 46. The digital data corresponding to the X-ray intensities are thence fed to a computer 47 and stored by the central processing unit (CPU) 48 of the computer 47 into a disk storage device 49. Typically each of the 180 detectors will be sampled 512 times during one linear scan across the body producing 92,160 digital measurements to be stored on the disk 49. The digitizer is driven by the master clock which derives its signal from photocell 33 so as to sample the output of detector array 22 at the appropriate positions in the scan. In order to compensate for the variations in the x-ray source intensity during the scan, x-ray detector 40, indicated in FIGS. 1, 2, and 3, monitors a portion of the x-ray beam which is stopped by collimator 13 and not transmitted to the body. The output of this detector is used with the x-ray monitor of FIG. 11 to insure that the computer has the corrected source strength.

The 92,160 measurements may be reconstructed by the CPU 48 to produce the desired 3-dimensional tomograph representing the distribution of X-ray attenuating or transmission coefficients.

The method of three dimensional reconstruction can be briefly explained as follows. The measurements are first preprocessed by taking the natural logarithm of each measurement and subtracting the logarithm of the unattenuated ray corresponding to a particular measurement as measured immediately before or after scanning through the body. These measurements are taken at the extremes of travel of the source 12 and detector 22 of FIG. 6 corresponding to measured values 36 and 37. This process can be represented mathematically as follows:

$$M_{ij} = \ln I_{ij} - \ln I_{oi} \qquad (Eq. 1)$$

where $M_{ij}$ is the corrected measurement of the $i^{th}$ beam measured at the $j^{th}$ source position, $I_{ij}$ is the actual measured current, and $I_{oi}$ is the unattenuated current value of the $i^{th}$ beam as corrected by x-ray monitor signal 40. $M_{ij}$ corresponds to the measured line integral of the linear attenuation or transmission coefficient along the $i,j^{th}$ ray. This relationship may be written as:

$$M_{ij} = -\int_{R_{ij}} \mu(x,y,z)ds \qquad (Eq. 2)$$

where $\mu$ is the linear attenuation coefficient and the integral represents line integration along the line represented by $R_{ij}$. The reconstruction problem is to solve the 92,160 integral equations for the unknown attenuation or transmission coefficients $\mu(x,y,z)$. The integral equation may be transformed to linear algebraic equations in the manner indicated in Eq. 3 below.

Referring now to FIG. 12, the continuous tomograph is represented by a two-dimensional matrix of picture elements, typically 256×256, containing $256^2$ values of $\mu(x,y,z)$. Each measurement $M_{ij}$ is represented by a ray $R_{ij}$ of width $w$ passing through this matrix. Thus equation (2) may be written as:

$$M_{ij} = \frac{1}{w} \sum_{k} f_{ijk} \mu_k \qquad (Eq. 3)$$

where $f_{ijk}$ is the fractional area of the $k^{th}$ picture element which is included within the ray of width $w$ along line $R_{ij}$. The $f_{ijk}$ are a series of known numbers determined geometrically and may be referred to as the cell fraction table. $f_{ijk}$ is equal to zero for picture elements or cells not intercepted by beam $R_{ij}$, and has a maximum value of one for those cells completely included within the beam. FIGS. 13 and 14 show the details of this cell interception in more detail.

The computer processing unit 48 must solve for the desired attenuation coefficients of each element $\mu_k$ given the processed projection measurements $M_{ij}$. This represents the classical problem of reconstruction from projections which has been treated extensively in the literature and has been implemented in a variety of commercial systems of computerized tomography. A review article on this subject is "Three Methods for Reconstructing Objects from X-Rays: A Comparative Study," by G. T. Herman and S. Rowland in *Computer Graphics and Image Processing*, Vol. 2, pp. 151–178, 1973.

In general all reconstruction approaches can be divided into two general categories, the direct and the iterative solutions. The direct methods, which will be considered first, make use of the fact that the Fourier transform of each projection forms a radial line in the two-dimensional Fourier transform of the desired reconstruction. Thus, given all of the projections, the complete Fourier transform of the $\mu_k$ values is known. The inverse transform then provides the desired $\mu_k$ reconstruction. This operation is often performed using its spatial equivalent with convolution and back projection.

In the case with linear scan, however, the complete Fourier transform of the desired $\mu_k$ reconstruction is not known since projections are not available over all 180°. A variety of approaches have been used to provide a diagnostically significant reconstruction with the limited data. One generalized approach involves analytic extension and is described in "Reconstruction of Three-Dimensional Refractive Index Fields from Multi-directional Interferometric Data," by D. W. Sweeney and C. M. Vest, *Applied Optics*, Vol. 12, pp. 2649–2664, 1973.

Here the missing region of the Fourier transform is filled in from the known data. With a finite object, its Fourier transform is analytic, so that unknown regions can be filled in by extensions from the known regions. The known regions must be known to a relatively high degree of accuracy since the extension process involves higher order derivatives.

Another direct approach is known as maximum entropy and is described in "Maximum Entropy Image Reconstruction," by S. J. Wernecke, Proc. of Image Processing for 2-D and 3-D Reconstructions From Projections; Theory and Practice in Medicine and the Physical Sciences, August 4–7, 1975, presented at Stanford, California. In this case, using the limited data, a reconstruction is made which maximizes the entropy of the image. This procedure automatically has the constraint that the reconstructed $\mu_k$ values must be non-negative.

The iterative techniques are very straightforward in that the desired $\mu_k$ values are iterated, using successive approximations, in order to find a set of $\mu_k$ values which match the $M_{ij}$ measured projections. The desirable characteristic of this method is that it is essentially the same whether or not data is taken over the entire 180° or a partial scan as in this case. Using the data available, the iterative technique finds the best fit. This method provides a diagnostically significant tomograph using data taken over approximately 90°.

The unknown $\mu_k$ may be determined from the linear algebraic equation (3) by means of an iterative technique of successive approximations as indicated by the following equation:

$$\mu'_k = \mu_k + \frac{f_{ijk}}{D W \sum_k f_{ijk}} \left( \sum_k f_{ijk} \mu_k - M_{ij} \right) \qquad (Eq. 4)$$

$k = 1 \dots k_{max}$
$i = 1 \dots n$
$j = 1 \dots m$ wherein the term in brackets represents a correction that is distributed over all the cells of the ray $R_{ij}$ in proportion to their fraction $f_{ijk}$ and weighted by a damping factor D. D may be determined experimentally and serves to reduce the required number of iterations. $\mu_k'$ is the approximation of $\mu_k$ after each iteration. This process is carried out for all values of the $i, j$ indices (all rays), and is repeated for multiple successive iterations. The starting values for $\mu_k$ may be zero, or preferably derived from the final reconstructed tomograph from an adjacent plane.

Although equation (4) represents a satisfactory algorithm for reconstructing limited angle shadowgraphs, it is apparent that many refinements are possible to fit particular applications. One refinement is to introduce constraints into the correction process based on prior information about the scanned object. A trivial example is that the $\mu_k$ values may be constrained to be positive numbers. Other refinements are discussed in the literature, such as the previously referenced review article by G. Herman, et. al.

One difficulty of the approach represented by equation (4) is that there are a large number of $f_{ijk}$ values to be calculated for each iteration. In the particular example discussed where $n=180$, $m=512$ and the matrix size is 256×256, approximately 40,000,000 non-zero values of $f_{ijk}$ exist. These may be calculated in advance and stored on a large disk file. It will become apparent that the size of this cell fraction table can be reduced to approximately 100,000 values by taking advantage of the built-in symmetry of the rectilinear scanner approach. Suppose the step size between successive source positions $s_j - S_{j+1} w$ is adjusted to coincide with the width of a matrix cell or an integer sub-multiple of cell spacing $d$ such as $d$, $d/2$, $d/3$, etc. Then upon referring to FIG. 14 it is apparent that the values of the sets of cell fractions $f_{ijk}$ for each beam $R_{ij}$ in one particular parallel ray shadowgraph, are equal and that the address of a particluar cell fraction $k$ is incremented by exactly +1 from the preceding ray. This symmetry may be represented as:

$$f_{ij+l, k+l} = f_{ijk} \quad \text{(Eq. 5)}$$

and this in effect reduces the storage requirement by a factor of 512. A further reduction by a factor of two in the stored cell fraction table is possible by taking advantage of the symmetry of a square image matrix about 90°. These improvements enable the ieterative algebraic reconstruction technique to remain competitive in cost and speed with convolution-back-projection methods employed on 180° rotary scanners. An added benefit of the iterative method is that it is relatively straight-forward to introduce non-linear corrections such as those needed to correct spectral shift artifacts.

FIG. 15 shows a flow chart of a typical reconstruction program based on these techniques. The actual FORTRAN listing of the computer program follows this description in Appendix A and should be referred to in reference to names of variables, subroutines, etc.

The first step shown in FIG. 15 is to calculate the cell fraction table and store it on tape or disk. This is performed by the program FRCTN2.FTN. The method of computation, briefly, is as follows. The subroutine GETFRP determines the intercepts of the left-hand and right-hand border of a particular beam with a particular cell. The subroutine BELOW calculates the triangular or trapezoidal area below a particular line within the cell of interest. The difference of these areas is the cell fraction $f_{ijk}$ referred to as RF(I,J) in the program. The subroutine BOUT writes the results on magnetic tape or a disk file in blocked format in order to optimize the speed of device reading. The index $k$ of the reconstruction matrix is stored immediately preceding the value of $f_{ijk}$ for that cell. Thus FR(N)=$k$, FR(N+1) = $f_{ijk}$, ... etc. A heading of ten words provides other information identifying the particular ray under consideration. The measure value of $M_{ij}$ is stored as the first element of this array by the associated data acquisition program.

The program HPLAR2.FTN may then be called to reconstruct the data MEASUR from a particular scan. The data is assumed to be sotred in the file described above along with the cell fraction table. Several options are available within the program HPLAR2.FTN. These options enable the selection of a water bag compensator, a conventional method of compensation wherein that portion of the body, i.e., head, etc, is enclosed by a water bag, if one is used during the scan, the use of a special damping factor [D in Eq. (4)] or others. The reconstruction matrix REC is dimensioned only 40 × 40 since the size of the particular computer used here was small. A preferred matrix size would be 256×256. Several other variables are also dimensioned to correspondingly small array sizes.

The basic iteration loop of this program precedes as decribed by Eq. (4). A simulated measurement through the reconstruction matrix is calculated ($\rho_k f_{ijk} \mu_k$). The difference between the simulated measurement and the actual measurement is then distributed back over all the values of $\mu_k$ within the particular beam. The process is continued for all rays and iterated approximately five times. The final result is stored in the matrix REC and is stored on the disk or tape file. A separate program can be used to display the matrix REC on a grey scale display 51 thus producing the tomographic image. Alternatively, the matrix REC may be printed on a line printer so that the actual absolute values of $\mu_k$ can be obtained.

FIG. 16 shows the manner in which several detector arrays 22 may be employed in order to scan several simultaneous planar tomographic slices. The manner of data acquisition and reconstruction is the same as previously described for a signle planar slice. The planes of various slices are tilted at small angles with respect to the axis of the patient, but all planes intercept the rectilinear line (locus of points) described by the moving source 12 and this guarantees that the data for each slice is exactly coplanar. In this manner an entire volumetric region, as illustrated in FIG. 16, is examined in a single rapid traverse of source 12. This is highly significant in many clinical studies, especially that of the heart. The study of diseased hearts is greatly facilitated by viewing the various planes throughout the volume which were taken at the same time. If these planes are acquired in sequence, they are very difficult to interpret because of the large motions involved. The existing computerized tomography scanners which employ rotational motion canot readily provide this volumetric capability. The data taken for regions outside the central plane is not organized in planar slices and is thus very difficult to reconstruct.

The limited scan angle feature, i.e., less than 180° with the present invention has several advantages and permits scanning configurations in which the x-ray source and fan X-ray beam or group of beamlets moves in a linear fashion and no rotation of the scanning apparatus is required. Such a scanning mode results in several advantages and improvements over the current art.

The advantages of linear computerized tomography versus translate-rotate tomography or rotary computerized tomography include higher scan speed, more compact size, lower cost, scan of saggital and coronal sections, and the ability to simulataneously image multiple slices. A disadvantage is that there is a loss of spatial resolution along the axis perpendicular to the direction of linear motion. In the case of linear computerized-tomography, this loss of resolution is compensated for by increasing the number of non-overlapping measurements obtained during the scan by various techniques including using a smaller sampling interval, more detectors and finer detector spacing.

Although the preferred locus of points for translation or lateral scan of the source 12 relative to the body 15 is rectilinear, this need not be the case. The only requirement being that the radius of curvature for the locus of points be substantially larger than the shortest distance from the center of the resultant 3-D tomograph to the source 12. In the limit, the radius of curvature is infinite corresponding to a straight line.

In some configurations a somewhat curved translation of the source might prove advantageous. This curved locus can provide an increase in the angular extent of the projection data. Using this curved locus, however, the off axis detectors, such as $A_1, A_2, A_4$ and $A_5$ in FIG. 16 will not represent a planar slice. However, for fairly large radii of curvature the departure from a planar slice will be negligible so that the entire volume can be reconstructed.

It is to be recognized that for a given position of the source 12 relative to the geometric center of the tomograph, the detectors 22 are detecting a shadowgram of divergent ray data and that as the source 12 moves from one extreme of travel to the other, for the scan, the relative angular position of the source 12 relative to the center of the tomograph changes for varying the scan angle so that each element of the tomographic matrix is intercepted by a set of intersecting ray paths. A tomographic reconstruction is preferably made by back-projecting sets of parallel ay data. Thus, the shadowgraphic sets of divergent ray data are preferably reordered into sets of parallel ray shadowgraphic data. It turns out that when the source 12 moves with the detectors 22 each detector detects, as a function of scan time, as set of parallel ray shadowgraphic data for each of a number of different scan angles. In this manner, the detected instantaneous divergent ray shadowgraphic data is reordered into parallel ray shadowgraphic data.

In the configurations shown thusfar the detector array 22 moved in synchronism with the source 12. In order to achieve the desired rapid scan the detector array 22 can remain stationary. In this way relatively few moving parts are involved since only the source 22 need be translated. In addition the reliability of detector array 22 would be improved since it would not be subject to the stress arising from rapid acceleration and vibration.

This fixed detector embodiment requires a longer detector since, as indicated in FIG. 6, the fixed detector must receive the rays from $R_1$ at the beginning of the scan to $R_n$ at the end of the scan. In addition, a focused grid collimator cannot be used since, at each detector position, rays arrive at a variety of angles. Thus a cost versus performance tradeoff must be evaluated between the mechanical simplicity of a fixed detector and its increased length and reduced ability to suppress scatter.

In stationary detector designs the collection of rays sequentially recorded by a single detector, unlike the moving detector case, do not correspond to a parallel ray shadowgraph. As shown in FIG. 5, in the moving detector case, detectors $D_1 \ldots D_n$, each produced parallel ray shadowgraphs corresponding to rays $R_1 \ldots R_n$. In the fixed detector case each detector element sequentially produces a divergent ray shadowgraph corresponding to all of the rays $R_1 \ldots R_n$ rather than a single ray. A preferred method of reconstructing these divergent ray shadowgraphs is the reordering into sets of parallel rays. This reordering is accomplished automatically with a moving detector. However the divergent ray shadowgraphic data can be stored in the computer and reordered into sets of parallel rays as described in U.S. Pat. No. 3,983,398.

As used in the claims appended hereto, "diagnostically significant" means that the reconstructed tomograph is of value to the radiologist or reviewer thereof in interpreting the interior structure of the region or planar slice of the body being examined. This will be the case if the reconstructed tomograph is not obscured by artifacts. These would be produced if reconstruction techniques employed in existing commercial tomographic scanners would be used on data acquired over limited angles. These obscuring artifacts can also result if the data acquired during a single lateral scan had an inadequate fan beam angle such as the fan angle of existing translaterotate scanners.

It is comtemplated that the X-ray source can be of the scanning electron beam type as described, for example, in West German laid-open application No. 2,538,517.

```
C
C
C     **************************************************************
C     **************************************************************
C     **************************************************************
C     ******                                                 ******
C     ******            PION TREATMENT PROJECT               ******
C     ******            DENSITY RECONSTRUCTION               ******
C     ******                                                 ******
C     ******            CELL FRACTION CALCULATION            ******
C     ******                 FRCTN2. FTN                     ******
C     ******                                                 ******
C     ******                 JIM DEHNERT                     ******
C     ******                 8 AUGUST, 1973                  ******
C     ******                                                 ******
C     **************************************************************
C     **************************************************************
C     **************************************************************
C
```

```
C      SETUP OF THE CELL FRACTION FILE FOR ALL OTHER PROGRAMS.
C
C      ***************************************************************
C      INPUT FOR THE PROGRAM IS AS FOLLOWS (ON PAPER TAPE):
C
C      FORMAT          DATA
C      ------          ----
C      2I5             NC, CINC
C      2I5             MEASUREMENT SET NUMBER
C      3F7.3,I3        XD, SD, PD, NP
C      ***************************************************************
C
       BLOCK DATA
       IMPLICIT INTEGER A, (F-P)
       COMMON /AT/ ATTR(40), MIN, MAX
       LOGICAL*1 FR(64, 64)
       COMMON /AR/ FR(64, 64)
       COMMON /IO/ LEN, PNT, OUT(350)
       COMMON /GF/ XX, XL, XU, YL, YU, TSIN, TCOS, XS, YS, XP0, YP0, ZC, SDS
       DATA ATTR /15*0, 2HPH, 2HAN, 2HTO, 2HM , 11*0, 2H   , 2HNO, 0, 0, 4, 5*0/
       DATA PNT /1/
       END

C
C
C      ***** MAIN PROGRAM BEGINS HERE *****
C
       IMPLICIT INTEGER (A-F), (H-Q)
C
       REAL PD
       COMMON /AT/ NC, CINC, AREA, NP, XD, SD, PD, NM, N, FT, MMAX, FMAX, HEAD(25),
      *            MIN, MAX
       INTEGER ATTR(15)
       EQUIVALENCE (ATTR(1), NC)
C
       LOGICAL*1 FR(64, 64)
       COMMON /AR/ FR(64, 64)
       LOGICAL*1 OUT(630)
       COMMON /IO/ LEN, PNT, CNT, AI, MI, FWT, IDISP, OUT(690)
       COMMON /GF/ XX, XL, XU, YL, YU, TSIN, TCOS, XS, YS, XP0, YP0, ZC, SDS
       REAL DTR
C
       REAL ABS, COS
       DATA SQRT2 /1.414213562/
C
       CALL SETFIL (2, 'FRACTN', IERR, 'MT')
       CALL SETFIL (8, 'TITLE2', IERR, 'SY')
       DEFINE FILE 8(12, 25, U, ATNO)
C
       DTR = 57.29578E0
       READ (4, 10) NC, CINC
  10   FORMAT (2I5)
       MAX = NC*CINC/2
       MIN = -MAX
       ZC = MIN-CINC/2.0
       AREA = CINC*CINC
       READ (4, 10) FT
       READ (4, 20) XD, SD, PD, NP
  20   FORMAT (3F7.3, I3)
       END FILE 4
       TD = 45.0/NP
       WRITE (5, 30) TD, XD
  30   FORMAT ('1ANGLES WILL BE AT', F5.2, ' DEGREE STEPS'/
      *        ' MEASUREMENTS WILL BE ', F5.1, ' MM WIDE.'//)
       IF (SD .NE. 0) WRITE (5, 40) SD, PD
  40   FORMAT (' A FAN-BEAM GEOMETRY WILL BE USED'/
      *        ' WITH THE SOURCE ', F5.1, ' MM FROM THE ORIGIN'/
      *        ' AND THE PROJECTION ', F5.1, ' MM FROM THE ORIGIN.'///)
       IF (SD .EQ. 0) WRITE (5, 50)
  50   FORMAT (' A PARALLEL-BEAM GEOMETRY WILL BE USED.'//)
       FMAX = 2.0*SQRT2*MAX
       NM = (FMAX/XD + 1.)/2.
       FMAX = FMAX*XD*100./AREA
       SDS = SD - SQRT2*MAX
       IF (SD .NE. 0.0) FMAX = FMAX*SDS/(SD+PD)
       AI = 0
```

```
    60     T = AI*45.0/DTR/NP
           IF ((AI .EQ. 0) .AND. (SD .EQ. 0.)) T = 1.57079632E0
           TSIN = SIN(T)
           TCOS = COS(T)
           IF (SD .NE. 0.) GO TO 70
           X = XD/TSIN
           GO TO 80
    70     X=XD
           NM=49
           XS = - SD * TCOS
           YS = -SD*TSIN
           XP0 = PD*TCOS
           YP0 = PD*TSIN
    80     Q = -NM
           DO 150 JK = 0,NM
           IF (JK .LE. -50) GO TO 150
           IF (JK .GE. 50) GO TO 150
           MI = JK+50
           XX = JK*X
           IF (SD .EQ. 0.) CALL GETFRP
           IF (SD .NE. 0.) CALL GETFRF
C
C          ***** CALCULATE WATER TANK FRACTION AND TRANSFER FR *****
           FWT = FMAX
           K = 1
           DO 140 J = 1,NC
           DO 140 I = 1,NC
           IF (FR(I,J) .EQ. 0) GO TO 140
           FWT = FWT - FR(I,J)
           IF (K .NE. 1) GO TO 130
           DISP = 64*J-64
           IDISP = DISP
   130     OUT(K) = 64*J-64+I-DISP
           DISP = DISP + OUT(K)
           OUT(K+1) = FR(I,J)
           K = K + 2
   140     CONTINUE
           LEN = K/2+6
           CNT = K-1
           IF (K .GT. 1) CALL BOUT(.FALSE.)
   150     CONTINUE
           AI = AI+1
           IF (AI .LE. NP) GO TO 60
           CALL BOUT(.TRUE.)
C
C          ***** OUTPUT SUMMARY DATA *****
           NPP1 = NP+1
           WRITE (5,200) NPP1
   200     FORMAT(///' CELL-FRACTION ARRAYS CALCULATED AT',I4,' ANGLES')
           WRITE (8'12) ATTR
           WRITE (8'1) HEAD
           END FILE 2
           END FILE 8
           REWIND 2
           STOP
           END
C
C
C GETFRP  GETFRP  GETFRP  GETFRP  GETFRP  GETFRP  GETFRP  GETFRP  GETFRP  GETFRP
C
           SUBROUTINE GETFRP
C
C          THIS ROUTINE, GIVEN A BEAM DETERMINED BY ITS ANGLE T (RADIANS)
C          WITH THE X-AXIS AND THE X-INTERCEPT XX OF ITS CENTER LINE,
C          DETERMINES A FRACTION ARRAY FR OF THE FRACTIONS OF EACH CELL
C          INCLUDED IN THE BEAM SWATH, SCALED FROM 0 TO 100.
C
           IMPLICIT INTEGER (A-F),(H-Q)
C
           COMMON /AT/ NC,CINC,AREA,NP,XD,ATTR(34),MIN,MAX
           BYTE FR(64,64)
           COMMON /AR/ FR(64,64)
           COMMON /GF/ XX,XL,XU,YL,YU,TSIN,TCOS
           COMMON /IO/ LEN,FNT,CNT,AI
           REAL COS
```

```
             TCOT = TCOS/TSIN
             XX2 = XD/TSIN
             XX1 = XX - XX2/2.
             XX2 = XX1 + XX2
             DO 150 I = 1, NC
             DO 150 J = 1, NC
      150    FR(I, J) = 0
             YU = MIN
             DO 240 J = 1, NC
             YL = YU
             YU = YU + CINC
             X1 = XX1 - YL*TCOT
             X2 = XX2 + YL*TCOT
             X3 = XX1 + YU*TCOT
             X4 = XX2 + YU*TCOT
             IF (X4 .LE. MIN) GO TO 240
             IF (X1 .GE. MAX) GO TO 250
             XU = MIN
             DO 200 I = 1, NC
             XL = XU
             XU = XU + CINC
             IF (X1 .GE. XU) GO TO 200
             IF (X4 .LE. XL) GO TO 240
             FR(I, J) = BELOW(X1, X3) - BELOW(X2, X4)
      200    CONTINUE
      240    CONTINUE
      250    IF (AI .NE. 0) RETURN
             Q = NC/2
             DO 300 I = 1, Q
             IX = Q+I
             IXN = Q-I+1
             DO 300 J = 1, Q
             IY = Q+I
             IYN = Q-J+1
             IT = FR(IX, IY)
             FR(IX, IY) = FR(IYN, IX)
             FR(IYN, IX) = FR(IXN, IYN)
             FR(IXN, IYN) = FR(IY, IXN)
      300    FR(IY, IXN) = IT
             RETURN
             END

C
C
C GETFRF    GETFRF    GETFRF    GETFRF    GETFRF    GETFRF    GETFRF    GETFRF    GETFRF
C
             SUBROUTINE GETFRF
C
C     THIS ROUTINE, GIVEN A BEAM DETERMINED BY THE POSITION OF THE SOURCE
C     AND THE POSITION OF THE CENTER OF ITS SECTION OF THE PROJECTION,
C     DETERMINES A FRACTION ARRAY FR OF THE FRACTIONS OF EACH CELL INCLUDED
C     IN THE BEAM SWATH, SCALED FROM 0 TO 100.
C
             IMPLICIT INTEGER (A-F), (H-Q)
C
             REAL PD
             COMMON /AT/ NC, CINC, AREA, NP, XD, SD, PD, DUM(30), MIN, MAX
             BYTE FR(64, 64), FRTMP
             COMMON /AR/ FR(64, 64)
             COMMON /GF/ XX, XL, XU, YL, YU, TSIN, TCOS, XS, YS, XP0, YP0, ZC, SDS
             COMMON /IO/ LEN, PNT, CNT, AI
             LOGICAL FLAG
C
C     NOTE THAT THE DISPLACEMENT COEFFICIENTS ALONG THE PROJECTION LINE
C     ARE GIVEN BY XPD=TSIN, YPD=-TCOS.
C
C     ***** CALCULATE THE PROJECTION POSITION *****
             X1 = XX-XD/2.
             X2 = X1+XD
             XP1 = TSIN*X1 + XP0 - XS
             XP2 = TSIN*X2 + XP0 - XS
             YP1 = -TCOS*X1 + YP0 - YS
             YP2 = -TCOS*X2 + YP0 - YS
             FLAG=. FALSE.
```

```
        IF (YP2 .GT. 0.) GO TO 50
        FLAG=.TRUE.
        TMP=XP1
        XP1=XP2
        XP2=TMP
        TMP=-YP1
        YP1=-YP2
        YP2=TMP
        YS=-YS
C
C       ***** ZERO THE ARRAY *****
   50   DO 100 I = 1,NC
        DO 100 J = 1,NC
  100   FR(I,J) = 0
        IF (FLAG .AND. (YP2 .LT. 0.)) RETURN
C
        YU = MIN-YS
        DO 240 J=1,NC
        YL=YU
        YU=YU+CINC
        IF (FLAG) ZY = ZC+J*CINC + YS
        IF (.NOT. FLAG) ZY = ZC+J*CINC - YS
        X1 = XS + XP1*YL/YP1
        X2 = XS + XP2*YL/YP2
        X3 = XS + XP1*YU/YP1
        X4 = XS + XP2*YU/YP2
  150   IF (X4 .LE. MIN) GOTO 240
        IF (X1 .GE. MAX) GO TO 250
        XU=MIN
        DO 200 I=1,NC
        XL=XU
        XU = XU + CINC

IF (X1 .GE. XU) GO TO 200
        IF (X4 .LE. XL) GO TO 240
        XC = ZC+I*CINC
        ZX=XC-XS
        SDST = SQRT(ZX*ZX+ZY*ZY)/SDS
        FR(I,J) = (BELOW(X1,X3)-BELOW(X2,X4))/SDST
  200   CONTINUE
  240   CONTINUE
  250   IF (.NOT. FLAG) RETURN
        YS=-YS
        DO 300 I=1,NC
        LIM=NC/2
        JJ=NC+1
        DO 300 J=1,LIM
        JJ=JJ-1
        FRTMP=FR(I,J)
        FR(I,J)=FR(I,JJ)
  300   FR(I,JJ)=FRTMP
        RETURN
        END

C
C
C BELOW  BELOW  BELOW  BELOW  BELOW  BELOW  BELOW  BELOW  BELOW  BELOW
C
        INTEGER FUNCTION BELOW(XA,XB)
C
C       THIS FUNCTION RETURNS THE FRACTION OF A CELL BELOW A LINE,
C       SCALED BETWEEN 0 AND 100, GIVEN THE LIMITS OF A CELL
C       XL,XU,YL,YU  AND THE X-VALUES XA AND XB WHERE A LINE PASSES
C       THROUGH THE HORIZONTAL LINES FORMING THE UPPER AND LOWER
C       BOUNDARIES OF THE CELL.
C
        IMPLICIT INTEGER (A-F),(H-Q)
C
        COMMON /AT/ NC,CINC
        COMMON /GF/ XX,XL,XU,YL,YU
C
        IF (XA .GE. XU) GO TO 100
        IF (XB .GT. XL) GO TO 10
C
```

```
C          ***** THE ENTIRE SQUARE IS BELOW THE LINE *****
           BELOW = 100
           RETURN
C
    10     IF (XB .GE. XU) GO TO 30
           IF (XA .GE. XL) GO TO 20
C
C          ***** SQUARE MINUS TRIANGLE IS BELOW LINE *****
           Y1 = (XB-XL)/(XB-XA)
           BELOW = 50.*(2.-Y1*(XB-XL)/CINC)
           RETURN
C
C          ***** A TRAPEZOID IS BELOW THE LINE *****
    20     BELOW = 50.*(2.*XU-XA-XB)/CINC
           RETURN
C
    30     Y2 = (XU-XA)/(XB-XA)
           IF (XA .GE. XL) GO TO 40
C
C          ***** A TRAPEZOID IS BELOW THE LINE *****
           Y1 = (XL-XA)/(XB-XA)
           BELOW = 50.*(Y1+Y2)
           RETURN
C
C          ***** A TRIANGLE IS BELOW THE LINE *****
    40     BELOW = 50.*(XU-XA)*Y2/CINC
           RETURN
C
C          ***** NO PART OF THE CELL IS BELOW THE LINE *****
    100    BELOW = 0
           RETURN
           END

C
C
C BOUT  BOUT  BOUT  BOUT  BOUT  BOUT  BOUT  BOUT  BOUT  BOUT
C
           SUBROUTINE BOUT(LAST)
C
           IMPLICIT INTEGER (A-F),(H-Q)
C
           COMMON /IO/ LEN,PNT,OUT(250)
           INTEGER BLOCK(960)
           LOGICAL LAST
C
           IF (.NOT. LAST) GO TO 100
C
C          ***** WE MUST OUTPUT THE LAST BLOCK *****
           BLOCK(PNT) = -1
           WRITE (2) BLOCK
           RETURN
    100    IF (PNT+LEN .LE. 960) GO TO 120
C
C          ***** WE CANNOT FIT ANOTHER RECORD ON THE CURRENT BLOCK *****
           BLOCK(PNT) = 0
           WRITE (2) BLOCK
           PNT = 1
C
C          ***** WE ARE NOW READY TO TRANSFER THE CURRENT RECORD *****
    120    Q = LEN - 1
           BLOCK(PNT) = LEN
           DO 140 I = 1,Q
    140    BLOCK(PNT+I) = OUT(I)
           PNT = PNT + LEN
           RETURN
           END

C
C
C RTAPE  RTAPE  RTAPE  RTAPE  RTAPE  RTAPE  RTAPE  RTAPE  RTAPE  RTAPE
C
           SUBROUTINE RTAPE
C
C          THIS SUBROUTINE READS THE NEXT FRACTION ARRAY OFF THE MAGNETIC
C          TAPE INTO THE ARRAY FR.
```

```
C
        IMPLICIT INTEGER (A-F),(H-Q),W
C
        COMMON /IO/ FR(2048),L,NO,PNT
        INTEGER BLOCK(1024)
        EQUIVALENCE (BLOCK(1),FR(1))
C
        REAL AR
        COMMON /ME/ MEAS,A,AR,SIGMA,SIG2,ZDAMP
        INTEGER ME(10)
        EQUIVALENCE (MEAS,ME(1))
C
        IF (L .NE. 1) GO TO 50
C
C       ***** FIRST RECORD - WE MUST OPEN FILE *****
        REWIND 7
   30   READ (7) BLOCK
        PNT = 1
        NO = BLOCK(1)
        GO TO 100
C
   50   PNT = PNT + NO + 1
        NO = BLOCK(PNT)
        IF (NO .EQ. 0) GO TO 30
C
C       ***** NOW WE CAN TRANSFER THE NEXT FRACTION ARRAY *****
  100   CONTINUE
        DO 150 I = 1,10
  150   ME(I) = BLOCK(PNT+I)
        RETURN
        END
```

```
C
C
C       ****************************************************
C       ****************************************************
C       ****************************************************
C       *****                                          *****
C       *****         PION TREATMENT PROJECT           *****
C       *****         DENSITY RECONSTRUCTION           *****
C       *****                                          *****
C       *****       HEPL ALGEBRAIC RECONSTRUCTION      *****
C       *****           AND ERROR ANALYSIS             *****
C       *****              HEPLAR.FTN                  *****
C       *****                                          *****
C       *****              JIM DEHNERT                 *****
C       *****            20 FEBRUARY, 1973             *****
C       *****                                          *****
C       ****************************************************
C       ****************************************************
C       ****************************************************
C
C
C       ****************************************************
C       INPUT FOR THE PROGRAM IS AS FOLLOWS (ON PAPER TAPE):
C
C       FORMAT          DATA
C       ------          ----
C       2L2,2I3         DAMP,SIGCOM,ITER,RECORD
C       25L1            ERROR(1::ITER)
C       ****************************************************
C
C       LINK WITH COMPAR.FTN, PRINT.FTN (LP OR KB)
C
C DATA
C       THE ATTRIBUTE ARRAY ATTR CONTAINS THE FOLLOWING VALUES:
C          ATTR(1) = NX = NUMBER OF CELLS IN THE X DIRECTION
C          ATTR(2) = INCX = X DIMENSION OF THE CELLS
C          ATTR(3) = NY = NUMBER OF CELLS IN THE Y DIRECTION
C          ATTR(4) = INCY = Y DIMENSION OF THE CELLS
C          ATTR(5) = AREA = AREA OF A SINGLE CELL
C          ATTR(6) = NP = NUMBER OF PROJECTION ANGLES
C          ATTR(7) = TD (REAL) = INCREMENT BETWEEN PROJECTION ANGLES
C          ATTR(9) = XD (REAL) = DISTANCE BETWEEN RAYS (CENTER LINES)
C          ATTR(11) = WIDTH = WIDTH OF RAYS
```

```
C       ATTR(12) = NM = NUMBER OF MEASUREMENTS AT EACH ANGLE
C       ATTR(13) = N = TOTAL NUMBER OF NON-ZERO MEASUREMENTS
C       ATTR(14) = MIND = MINIMUM DIMENSION FOR SCAN ROUTINE
C       ATTR(15) = MAXD = MAXIMUM DIMENSION FOR SCAN ROUTINE
C       ATTR(16)-ATTR(26) = IDIV(1)-IDIV(11) =
C            BREAKPOINTS FOR SCAN ROUTINE ENCODING OF DENSITY
C       ATTR(27) = TANK = BLANK IF WATER TANK USED - "NO" OTHERWISE
C       ATTR(28) = SCATTER = ANGLES SCATTERED? - SAME CODING AS TANK
C       ATTR(29) = PHAN = ID NUMBER OF PHANTOM
C       ATTR(30) = BLANK
C   L IS THE NUMBER OF THE MEASUREMENT CURRENTLY BEING CONSIDERED
C   NO IS THE LENGTH OF THE CURRENT CELL FRACTION ARRAY (FR)
C   FR CONTAINS THE REDUCED CELL FRACTION ARRAY AND THE FOLLOWING:
C       FR(1) = MEAS = THE RETURNED MEASUREMENT
C       FR(2) = A = BLANK NOW - USED IN GOITEIN RECONSTRUCTION
C       FR(3) = AR = PART OF MEASUREMENT RESULTING FROM WATER TANK
C       FR(5) = SIGMA = STANDARD DEVIATION OF THE MEASUREMENT ERROR
C       FR(7) = SIG2 = 1/(SIGMA*SIGMA)
C       FR(9) = ZDAMP = SPECIAL DAMPING FACTOR FOR EMI RECONSTRUCTION
C
C
C
C
C
C
C
C       FR(11::310) = REDUCED FRACTION ARRAY
C   DEN IS THE ARRAY CONTAINING THE DENSITY OF THE ORIGINAL PHANTOM
C   REC IS THE RECONSTRUCTED DENSITY ARRAY
C   RECS IS AN ALTERNATIVE INDEXING SCHEME (1-DIM) FOR REC
C   THE HEADING ARRAY HEAD CONTAINS:
C       HEAD(1::15) = ARRAY TITLE
C       HEAD(16) = TANK (WORD "NO" OR BLANK)
C       HEAD(17) = SCATTER (SAME CODE AS TANK)
C       HEAD(18) = PHANTOM NUMBER
C       HEAD(19) = ITERATION NUMBER
C       HEAD(20) = WORD COUNT FOR TITLE
C       HEAD(21) = TIME ELAPSED IN RECONSTRUCTION
C       HEAD(22) = SPECIAL DAMPING (SAME CODE AS TANK)
C       HEAD(23) = SIGMA COMPARISON (SAME CODE AS TANK)
C       HEAD(24::25) = BLANK
C
        BLOCK DATA
        IMPLICIT INTEGER (A-F),(H-Q),W
        COMMON /AT/ ATTR(30)
        COMMON /IO/ FR(2048),L,NO,PNT
        REAL AR
        COMMON /ME/ MEAS,A,AR,SIGMA,SIG2,ZDAMP
        INTEGER REC(40,40)
        COMMON /AR/ HEAD(25),REC(40,40),DEN(40,40)
        DATA HEAD/2HHE,2HPL,2H  ,2HAL,2HGE,2HBR,2HAI,2HC ,2HRE,2HCO,
     *       2HNS,2HTR,2HUC,2HTI,2HON,0,0,0,0,15,0,0,0,0,0/
        END

C
C
C  ****************************************************************
C  ****************************************************************
C  *****                                                      *****
C  *****              RECONSTRUCTION                          *****
C  *****                                                      *****
C  ****************************************************************
C  ****************************************************************
C
        IMPLICIT INTEGER (A-F),(H-Q),W
C
        COMMON /AT/ ATTR(30)
        EQUIVALENCE (ATTR(1),NX), (ATTR(2),INCX), (ATTR(3),NY),
     *  (ATTR(4),INCY),(ATTR(5),AREA),(ATTR(6),NP),(ATTR(7),TD),
     *  (ATTR(9),XD),(ATTR(11),WIDTH),(ATTR(12),NM),(ATTR(13),N)
        INTEGER REC(40,40),RECX(1600)
        COMMON /AR/ HEAD(25),REC(40,40),DEN(40,40)
        EQUIVALENCE (REC(1,1),RECX(1))
        COMMON /IO/ FR(2048),L,NO,PNT
        REAL AR
        COMMON /ME/ MEAS,A,AR,SIGMA,SIG2,ZDAMP
```

```
C
C        DAMP AND SIGCOM ARE FLAGS INDICATING WHETHER OR NOT WE ARE TO
C              USE THE SPECIAL DAMPING AND SIGMA COMPARISON,
C              RESPECTIVELY, IN OUR RECONSTRUCTION.
C        DMP AND COM CORRESPOND TO DAMP AND SIGCOM AND CONTAIN EITHER
C              THE WORD 'NO' OR BLANKS, AS APPROPRIATE.
C        RECORD AND RECRD1 ARE THE RECORD NUMBERS OF THE FIRST AND LAST
C              RECONSTRUCTIONS, RESPECTIVELY, OUTPUT TO DISK FOR
C              COMPARISON.
C        ERROR(25) IS AN ARRAY OF FLAGS INDICATING WHETHER OR NOT THE
C              RECONSTRUCTION FROM A PARTICULAR RECONSTRUCTION IS TO BE
C              OUTPUT TO DISK FOR LATER ERROR ANALYSIS.
C        ZDMP CONTAINS THE NORMAL DAMPING FACTOR FOR USE IF DAMP=.FALSE.
C
         LOGICAL DAMP, SIGCOM
         INTEGER DMP, COM
         INTEGER RECORD, RECRD1
         LOGICAL ERROR(25)
         REAL COR, DUM, ABS
C
C        ***** SET UP FILES *****
         CALL SETFIL(1, 'ARRAYS', IERR, 'DK')
         CALL SETFIL(2, 'ATTRIB', IERR, 'DK')
         CALL SETFIL(4, 'A', IERR, 'PR')
         CALL SETFIL(5, 'A', IERR, 'KB')
         CALL SETFIL(7, 'MEASR1', IERR, 'DK')
         CALL SETFIL(8, 'TITLES', IERR, 'DK')
         DEFINE FILE 1(11, 1600, U, ARNO)
         DEFINE FILE 8(11, 25, U, ATNO)
C
C        ***** INITIALIZATION *****
         READ (2) ATTR
         ZDMP = 1.*INCX/WIDTH
         DO 10 I = 16, 18
   10    HEAD(I) = ATTR(11+I)
         AMAX=SQRT(NX*NX*INCX*INCX+NY*NY*INCY*INCY*1.0) * WIDTH
C
C        ***** READ TYPE OF RECONSTRUCTION,
C                    NUMBER OF ITERATIONS, AND
C                    RECORD NUMBER OF FIRST OUTPUT ARRAY
         READ (4, 20) DAMP, SIGCOM, ITER, RECORD
   20    FORMAT (2L2, 2I3)
         DMP = 2HNO
         IF (DAMP) DMP = 2H
         COM = 2HNO
         IF (SIGCOM) COM = 2H
         HEAD(22) = DMP
         HEAD(23) = COM
         ARNO = RECORD
         ATNO = RECORD
         IF (.NOT. (DAMP .OR. SIGCOM)) HEAD(3) = 2HA
         IF (DAMP .AND. (.NOT. SIGCOM)) HEAD(3) = 2HB
         IF ((.NOT. DAMP) .AND. SIGCOM) HEAD(3) = 2HC
         IF (DAMP .AND. SIGCOM) HEAD(3) = 2HD
C
C        ***** READ ERROR ANALYSIS FLAG ARRAY *****
         READ (4, 30) (ERROR(I), I=1, ITER)
   30    FORMAT (25L1)
         END FILE 4
C
C        ***** INITIALIZE DENSITY ARRAY *****
         DO 40 I=1, NX
         DO 40 J=1, NY
   40    REC(I, J) = 1000
C
C        ***** ENTER THE ITERATION LOOP *****
         DO 300 LL = 1, ITER
         NCHG = 0
         CALL TIME (Q1, Q2)
         RTIME = 32768.0*Q1 + Q2
         HEAD(19) = LL
         REWIND 7
C
C        ***** PROCESS EACH MEASUREMENT *****
         DO 200 L = 1, N
```

```
C
C       ***** READ MEASUREMENT DATA, REDUCED CELL FRACTION ARRAY *****
        CALL RTAPE
C
C       ***** SIMULATE A MEASUREMENT THROUGH THE RECONSTRUCTED ARRAY *****
        Q1 = PNT + 11
        Q2 = PNT + NO

T1 = 0.
        DO 50 K = Q1, Q2, 2
  50    T1 = T1 + 1.*FR(K+1)*RECX(FR(K))
        T1 = T1*1.0E-6

C
        XL = AREA*T1 + AR
        DUM = AMAX - AR*.1
        IF (DUM .LT. 1.0E-5) GO TO 200
C
C       ***** CHECK FOR SPECIAL DAMPING *****
        IF (.NOT. DAMP) ZDAMP = ZDMP
C
C       ***** CHECK FOR SIGMA COMPARISON *****
        IF (.NOT. SIGCOM) GO TO 160
        COR = ABS(MEAS-XL)
        IF (COR-SIGMA) 200,200,140
 140    IF (COR-SIGMA*2.) 150,160,160
 150    COR = (MEAS-XL)*AREA*ZDAMP*.0002*(COR-SIGMA)/(COR*DUM)
        GO TO 180
 160    COR = (MEAS-XL)*AREA*ZDAMP*.0001/DUM
C
C       ***** MAKE THE CORRECTIONS *****
 180    NCHG = NCHG + 1
C
        DO 190 K = Q1, Q2, 2
 190    RECX(FR(K)) = RECX(FR(K)) + COR*FR(K+1)

C
 200    CONTINUE
        NCHG = NCHG*100./N
        CALL TIME(Q1, Q2)
        RTIME = (32768.0*Q1 + Q2 - RTIME)/60.0
        HEAD(21) = RTIME
C
C       ***** OUTPUT RECONSTRUCTION *****
        CALL HEADIN(.TRUE.)
        WRITE (5,250) DMP, COM
        CALL SCAN(REC)
        CALL HEADIN(.TRUE.)
        WRITE (5,250) DMP, COM
        CALL PRINT(REC)
 250    FORMAT (' (WITH ',A2,' SPECIAL DAMPING; WITH ',A2,
       *        ' SIGMA CORRECTION)'/)
        WRITE (5,270) RTIME, NCHG
 270    FORMAT (/'0',F6.1,' SECONDS ELAPSED IN RECONSTRUCTION.'/
       *         ' ',I3,'% OF MEASUREMENTS RESULTED IN ADJUSTMENT.')
        IF (.NOT. ERROR(LL)) GO TO 300
        WRITE (1'ARNO) REC
        WRITE (8'ATNO) HEAD
 300    CONTINUE
C
C       ***** PERFORM COMPARISON WITH ORIGINAL PHANTOM *****
        RECRD1 = ARNO-1
        READ (8'1) HEAD
        READ (1'1) DEN
        CALL HEADIN(.FALSE.)
        CALL SCAN(DEN)
        CALL HEADIN(.FALSE.)
        CALL PRINT(DEN)
        DO 400 I = RECORD, RECRD1
        READ (1'I) REC
        READ (8'I) HEAD
 400    CALL COMPAR
C
```

```
C       ***** WE MUST FINALLY CLOSE THE FILES *****
        END FILE 1
        END FILE 2
        END FILE 7
        END FILE 8
        REWIND 7
        STOP
        END

C
C
C       ********************************************************************
C       ********************************************************************
C       ********************************************************************
C       *****                                                          *****
C       *****              PION TREATMENT PROJECT                      *****
C       *****              DENSITY RECONSTRUCTION                      *****
C       *****                                                          *****
C       *****              CELL FRACTION INPUT AND                     *****
C       *****              ERROR ANALYSIS ROUTINES                     *****
C       *****                    COMPR2.FTN                            *****
C       *****                                                          *****
C       *****                    JIM DEHNERT                           *****
C       *****                  21 AUGUST, 1973                         *****
C       *****                                                          *****
C       ********************************************************************
C       ********************************************************************
C       ********************************************************************
C
C
C
C
C COMPARE   COMPARE   COMPARE   COMPARE   COMPARE   COMPARE   COMPARE   COMPARE
C
        SUBROUTINE COMPAR
C
C       THIS ROUTINE, GIVEN THE DENSITY ARRAY DEN OF AN ACTUAL
C       PHANTOM AND A RECONSTRUCTED DENSITY ARRAY REC, RETURNS A
C       STATISTICAL COMPARISON OF THE TWO.
C
C       MAJOR VARIABLES USED ARE:
C          RMSM  = RMS ERROR OF THE MEASUREMENTS
C          RMSMP = RMS PERCENTAGE ERROR OF THE MEASUREMENTS
C          CHI   = CHI-SQUARED ERROR OF THE MEASUREMENTS
C          CHIP  = CHI-SQUARED ERROR PER DEGREE OF FREEDOM
C          RMSD  = RMS ERROR OF THE CELL DENSITIES
C          RMSDP = RMS PERCENTAGE ERROR OF THE CELL DENSITIES
C          R     = MEAN RELATIVE ABSOLUTE ERROR OF THE CELL DENSITIES
C
        IMPLICIT INTEGER (A-F),(H-Q)
C
        LOGICAL OP
        COMMON /AT/ NC,CINC,AREA,NP,DUM(6),NM,N,DU2(27),OP
        INTEGER REC(64,64)
        COMMON /AR/ HEAD(25),REC(64,64),DEN(64,64)
        COMMON /IO/ L,FR(495)
        COMMON /ME/ MEAS,MWT,SIGMA,SIG2
C
        REAL RMSM,RMSMP,CHI,CHIP,RMSD,RMSDP,R,RD
C
C       ***** PERFORM ANALYSIS OF MEASUREMENTS *****
        REWIND 2
        REWIND 3
        RMSM = 0.
        RMSMP = 0.
        CHI = 0.
        DO 100 L = 1,N
        CALL GETM
        CALL MCALCM(REC,XL)
        XL = XL+MWT
        X = (XL-MEAS)*(XL-MEAS)
        RMSM = X + RMSM
        IF (MEAS.LT.3) GO TO 100
        RMSMP = X/MEAS/MEAS + RMSMP
        CHI = X*SIG2 + CHI
100     CONTINUE
```

```
              RMSM = SQRT(RMSM/N)
              RMSMP = SQRT(RMSMP/N)
              CHIP = CHI/N
C
C             ***** OUTPUT RECONSTRUCTED PHANTOM *****
              CALL HEADIN(.TRUE.,.FALSE.)
              CALL SCAN(REC)
              CALL HEADIN(.TRUE.,.TRUE.)
              CALL PRINT(REC)
              IF (.NOT. OP) WRITE (5,300) HEAD(19)
     300      FORMAT ('1AFTER ITERATION #',I2,':')
C
C             ***** PERFORM ANALYSIS OF RECONSTRUCTED PHANTOM *****
              IF (.NOT. OP) GO TO 750
              DO 400 I = 1,NC
              DO 400 J = 1,NC
     400      REC(I,J) = REC(I,J) - DEN(I,J)
              CALL SSWTCH (0,I)
              IF (I .EQ. 2) GO TO 550
              WRITE (5,500)
     500      FORMAT('1THE RECONSTRUCTION ERROR ARRAY IS:'//)
              CALL PRINT(REC)
     550      RMSD = 0.
              RMSDP = 0.
              R = 0.
              RD = 0.
              DO 600 I = 1,NC
              DO 600 J = 1,NC
              X = IABS(REC(I,J))
              RMSD = RMSD + X*X
              RMSDP = RMSDP + X*X/DEN(I,J)/DEN(I,J)
              R = R + X
     600      RD = RD + DEN(I,J)
              R = R/RD
              RMSD = SQRT(RMSD/NC/NC)
              RMSDP = SQRT(RMSDP/NC/NC)
C
C             ***** OUTPUT SUMMARY DATA *****
              WRITE (5,300) HEAD(19)
              WRITE (5,700) RMSD,RMSDP,R
     700      FORMAT('0THE RMS DENSITY ERROR IS',F7.0,','//
    *                ' AND THE RELATIVE RMS ERROR IS ',F6.4/
    *                '0THE MEAN RELATIVE ABSOLUTE ERROR IS',F6.4/)
     750      WRITE (5,900) RMSM,RMSMP,CHI,CHIP,HEAD(21)
     900      FORMAT('0THE RMS ERROR OF THE RECONSTRUCTION MEASUREMENTS IS',
    *                F7.0,','// ' AND THE RELATIVE RMS ERROR IS ',F6.4/
    *                '0THE CHI-SQUARED ERROR IS ',E12.5,','//
    *                ' WHICH IS ',F7.2,' PER DEGREE OF FREEDOM.'//
    *                '0THE ELAPSED TIME IN COMPUTATION WAS ',I3,' SECONDS.'/)
              RETURN
              END
C
C
C
C GETF     GETF    GETF    GETF    GETF    GETF    GETF    GETF    GETF    GETF    GETF
C
              SUBROUTINE GETF
C
C             THIS SUBROUTINE READS THE NEXT FRACTION ARRAY INTO THE ARRAY FR.
C
              IMPLICIT INTEGER (A-F),(H-Q)
C
              COMMON /IO/ L,CNT,AI,MI,FWT,IDISP,FR(490)
              INTEGER BLOCK(960)
C
              IF (L .NE. 1) GO TO 50
C
C             ***** FIRST RECORD - MUST OPEN FILE *****
              MTYPE=1
              READ (2) BLOCK
              PNT=1
C
C             ***** TRANSFER THE NEXT FRACTION ARRAY *****
     50       CALL MGETF (BLOCK,PNT,NO,MTYPE)
C
```

```
C            *****  READ A NEW RECORD IF NECESSARY  *****
             IF (NO .NE. -1) GO TO 100
             REWIND 2
             IF (MTYPE .EQ. 4) RETURN
             NO=0
             MTYPE = MTYPE+1
     100     IF (NO .NE. 0) RETURN
             READ (2) BLOCK
             PNT=1
             RETURN
             END

C
C
C GETM    GETM    GETM    GETM    GETM    GETM    GETM    GETM    GETM    GETM    GETM
C
             SUBROUTINE GETM
C
C            THIS SUBROUTINE READS THE NEXT FRACTION ARRAY AND MEASUREMENT
C            INTO THE ARRAYS FR AND MIPT.
C
             IMPLICIT INTEGER (A-F),(H-Q)
C
             COMMON /IO/ L,CNT,AI,MI,FWT,IDISP,FR(490)
             COMMON /ME/ MEAS,MWT,SIGMA,SIG2
             COMMON /MA/ MS(100),MW(100),SG(100),S2(100)
             INTEGER MIPT(600)
             EQUIVALENCE (MIPT(1),MS(1)),(MS(100),AIM)
C
             IF (L .NE. 1) GO TO 50
C
C            *****  FIRST RECORD - WE MUST OPEN FILE  *****
             READ (3) MIPT
             AI = 0
C
C            *****  TRANSFER THE NEXT MEASUREMENT  *****
     50      AIT = AI
             CALL GETF
             IF (AI .NE. AIT) READ (3) MIPT
     60      IF (AIM .EQ. AI) GO TO 80
C
C            *****  WE MUST SKIP AN ANGLE OF CELL FRACTIONS  *****
             AIT=AI
     70      CALL GETF
             IF (AI .EQ. AIT) GO TO 70
             GO TO 60
     80      MEAS = MS(MI)
             MWT = MW(MI)
             SIGMA = SG(MI)
             SIG2 = S2(MI)
             RETURN
             END

C
C
C            ************************************************************
C            ************************************************************
C            ************************************************************
C            ******                                                ******
C            ******           PION TREATMENT PROJECT               ******
C            ******           DENSITY RECONSTRUCTION               ******
C            ******                                                ******
C            ******         DENSITY ARRAY PRINT ROUTINES           ******
C            ******                 PRINT2.FTN                     ******
C            ******                                                ******
C            ******                 JIM DEHNERT                    ******
C            ******               1 AUGUST, 1973                   ******
C            ******                                                ******
C            ************************************************************
C            ************************************************************
C            ************************************************************
C
C
C HEADING    HEADING    HEADING    HEADING    HEADING    HEADING    HEADING
C
```

```
        SUBROUTINE HEADIN(ITERAT,CHECK)
C
C       THIS SUBROUTINE PRINTS AN ARRAY HEADING AT THE TOP OF A NEW PAGE,
C       GIVEN THE HEADING DATA IN THE ARRAY HEAD, AND INSTRUCTIONS
C       CONCERNING WHETHER OR NOT TO PRINT ITERATION NUMBER INFORMATION
C       (THE ITERAT PARAMETER) AND WHETHER OR NOT TO PRINT THE HEADING
C       IF CONTROL PANEL SWITCH 0 IS IN THE SUPPRESS (UP) POSITION
C       (THE CHECK PARAMETER).
C
        IMPLICIT INTEGER (A-F),(H-Q)
C
        INTEGER HEAD(25)
        COMMON /AR/ HEAD(25)
        LOGICAL ITERAT,CHECK
C
        CALL SSWTCH(0,Q)
        IF ((Q .EQ. 2) .AND. (CHECK)) RETURN
C
        Q = HEAD(20)
        WRITE (5,300) HEAD(18),HEAD(16),HEAD(17)
300     FORMAT ('1PHANTOM #',I1,' WITH ',A2,' WATER TANK, ',A2,
     *          ' ANGLE SCATTERING.')
        IF (ITERAT) WRITE (5,310) HEAD(19),(HEAD(I),I=1,Q)
310     FORMAT (' AFTER ITERATION #',I2,', THE ',15A2,' IS:'/)
        IF (.NOT. ITERAT) WRITE (5,320) (HEAD(I),I=1,Q)
320     FORMAT (' THE ',15A2,' IS:'/)
        RETURN
        END

C
C
C SCAN   SCAN   SCAN   SCAN   SCAN   SCAN   SCAN   SCAN   SCAN   SCAN   SCAN
C
        SUBROUTINE SCAN(A)
C
C       THIS ROUTINE PRINTS A DENSITY PLOT OF THE ARRAY A.
C          VALUES BELOW MIND ARE PLOTTED AS BLANKS
C          VALUES ABOVE MAXD ARE PLOTTED AS ASTERISKS (*)
C          VALUES BETWEEN THOSE LIMITS ARE DIVIDED INTO 10 INTERVALS
C               AND PLOTTED AS 0,1,2,3,4,5,6,7,8,9.
C
        IMPLICIT INTEGER (A-F),(H-Q)
C
        COMMON /AT/ NC,ATTR(18),DIV(18),MIND,MAXD
C
        INTEGER TRIM
        DIMENSION A(64,64)
        DIMENSION P(66),CHAR(12)
        DATA CHAR /1H ,1H0,1H1,1H2,1H3,1H4,1H5,1H6,1H7,1H8,1H9,1H*/
        DATA TRIM /1H+/
C
        WRITE (5,5) NC,NC,MIND,MAXD
5       FORMAT ('0THE DIMENSIONS OF THE PHANTOM GRID ARE',I3,' BY',I3/
     *          ' THE NUMBERED INTERVALS LIE BETWEEN',I5,' AND',I5/)
        LIM = NC + 2
        P(1) = TRIM
        P(LIM) = TRIM
        WRITE (5,25) (TRIM,I=1,LIM)
25      FORMAT (' ',66A1)
        DO 60 JJ = 1,NC
        J = NC+1-JJ
        DO 40 I = 1,NC
        DO 30 K = 1,11
        IF (A(I,J) .GE. DIV(K)) GO TO 30
        P(I+1) = CHAR(K)
        GO TO 40
30      CONTINUE
        P(I+1) = CHAR(12)
40      CONTINUE
60      WRITE (5,25) (P(I),I=1,LIM)
        WRITE (5,25) (TRIM,I=1,LIM)
        RETURN
        END
```

```
C
C
C   PRINT    PRINT    PRINT    PRINT    PRINT    PRINT    PRINT    PRINT    PRINT
C
          SUBROUTINE PRINT(A)
C
C         THIS SUBROUTINE PRINTS THE DENSITY ARRAY A.
C
          IMPLICIT INTEGER (A-F),(H-Q)
C
          COMMON /AT/ NC
          INTEGER A(64,64)
C
          CALL SSWTCH(0,K)
          IF (K .EQ. 2) GO TO 80
          K = 1
          COL = 0
   20     IF (NC .LE. COL) GO TO 80
          BEGIN = COL + 1
          COL = COL + 15
          IF (NC .LT. COL) COL = NC
          WRITE (5,30) K,(I,I=BEGIN,COL)
   30     FORMAT (///I6,15I5)
          WRITE (5,40)
   40     FORMAT ('+SECT'/)
          DO 50 JJ = 1,NC
          J = NC + 1 - JJ
   50     WRITE (5,30) J,(A(I,J),I=BEGIN,COL)
          K = K + 1
          GO TO 20
   80     RETURN
          END
```

What is claimed is:

1. An apparatus for examining a region of the interior of a body using penetrating radiation comprising:
   source means for directing a divergent beam of penetrating radiation through the region of the body to be examined, said penetrating radiation being directed through the region of the body over a plurality of divergent paths for a given position of said source means relative to the body;
   detector means for detecting the transmitted radiation that has passed through the region of the body at a number of positions within the angle subtended by the divergent radiation beam for each of a plurality of lateral positions of said source means relative to the body to thereby provide a set of data corresponding to the transmission of the penetrating radiation at the number of positions within the angle subtended by the divergent beam for each of the plurality of lateral positions of said source means relative to the region of the body being examined;
   means for laterally scanning said source means such that the divergent beam is scanned once across the lateral extent of the region of the body being examined;
   means for processing the plurality of sets of data from the single lateral scan of said source means relative to the region of the body being examined to provide an attenuation coefficient for each of a plurality of individual matrix elements corresponding to the region of the body being examined; and
   means to display the matrix of attenuation coefficients to thereby provide a diagnostically significant three-dimensional tomograph of the region of the body being examined, said divergent beam being of sufficient angular spread to provide data from which a diagnostically significant tomograph can be obtained.

2. The apparatus of claim 1 wherein said detector means is laterally scanned in synchronism with said source means so that each element of the detector means detects the transmitted radiation from a specific ray path of the divergent beam.

3. The apparatus of claim 2 wherein said lateral scanning means causes said source means and said detector means to laterally scan the region of the body in a manner which is substantially free of relative rotary movement between (a) the region of the body and (b) said source means and said detector means.

4. The apparatus of claim 1 wherein said lateral scanning means causes said source means to laterally scan the region of the body in a manner which is substantially free of rotary movement of said source means about the region of the body being examined.

5. The apparatus of claim 1 wherein the region of the interior of the body being examined is a planar slice, the divergent beam is a planar fan-shaped beam and the detector means is a linear array of detector elements intercepting the transmitted planar fan-shaped beam.

6. The apparatus of claim 1 wherein the region of the interior of the body being examined is a plurality of planar slices within the divergent beam and the detector means is a plurality of linear detector arrays, each of the detector arrays intercepting the transmission of the divergent beam through different planar slices.

7. The apparatus of claim 1 wherein the angle subtended by the divergent beam of radiation is approximately 90°.

8. The apparatus of claim 1 wherein the angle subtended by the divergent beam of radiation is about 60° to about 130°.

9. The apparatus of claim 1 wherein the beam of divergent radiation is totally outside the region of the body at each extreme of travel of the lateral scan.

10. The apparatus of claim 1 wherein at least about 50% of the beam of divergent radiation is outside the region of the body at each extreme of travel of the lateral scan.

11. The apparatus of claim 1 further including means between said source means and the body for radially collimating the divergent beam of radiation into a plurality diverging beamlets of radiation.

12. The apparatus of claim 11 further including means, disposed between the body and said detector means, for radially collimating the radiation emerging from the body.

13. The apparatus of claim 1 wherein said divergent beam of radiation, as directed onto the body, is of generally continuous uniform intensity across the angle subtended thereby.

14. The apparatus of claim 1 wherein the means for laterally scanning said source means provides motion along a rectilinear path.

15. The apparatus of claim 1 wherein the means for laterally scanning said source means provides motion along an arc of a circular path whose radius of curvature is substantially larger than the distance from the source to the center of the region of the body being examined.

16. The apparatus of claim 1 wherein said detector means remains stationary during the lateral scanning by said source means.

17. A method for examining a region of the interior of a body using penetrating radiation comprising:
 directing a divergent beam of penetrating radiation from a source through the region of the body to be examined over a plurality of divergent paths for a given position of the source relative to the body;
 translating the source such that the divergent beam is scanned once across the lateral extent of the region of the body being examined;
 detecting the transmitted radiation that has passed through the region of the body at a number of spaced positions within the angle subtended by the divergent radiation beam for each of a plurality of lateral positions of the source relative to the body to thereby provide a set of data corresponding to the transmission of the penetrating radiation at the number of positions within the angle subtended by the divergent beam for each of the plurality of lateral positions of the source relative to the body;
 processing the plurality of sets of data from the single lateral scan of the source relative to the body to provide an attenuation coefficient for each of a plurality of individual matrix elements corresponding to the region of the body being examined; and
 displaying the matrix of attenuation coefficients to thereby provide a diagnostically significant three-dimensional tomograph of the region of the body being examined.

18. The method of claim 17 wherein translation of the source occurs along a rectilinear path.

19. The method of claim 17 wherein the translation of the source occurs along an arc of a circular path whose radius of curvature is substantially larger than the distance from the source to the center of the region of the body being examined.

20. The method of claim 17 wherein the region of the body being examined is a planar slice and the divergent beam is a planar fan-shaped beam.

21. The method of claim 17 wherein the beam of divergent radiation is totally outside the region of the body at each extreme of travel of the lateral scan.

22. The method of claim 17 wherein at least about 50% of the beam of divergent radiation is outside the region of the body at each extreme of travel of the lateral scan.

23. The method of claim 17 wherein the divergent beam of radiation is radially collimated into a plurality of radially diverging beamlets of radiation.

24. The method of claim 17 wherein the divergent beam of radiation, as directed onto the body, is of generally continuous uniform intensity across the angle subtended thereby.

25. The method of claim 24 further including radially collimating the radiation emerging from the body.

26. The method of claim 17 wherein the divergent beam has sufficient angular spread to provide data from which a diagnostically significant tomograph can be obtained.

27. The method of claim 17 wherein the lateral scanning of the beam is substantially free of rotary movement of the beam of radiation about the region of the body being examined.

28. The method of claim 17 wherein the lateral scanning of the beam is substantially free of relative rotary movement between (a) the region of the body and (b) the beam of radiation.

29. The method of claim 26 wherein the angle subtended by the divergent beam of radiation is approximately 90°.

30. The method of claim 26 wherein the angle subtended by the divergent beam of radiation is about 60° to about 130°.

* * * * *